(12) United States Patent
Magliocco

(10) Patent No.: US 11,360,094 B2
(45) Date of Patent: Jun. 14, 2022

(54) METHOD FOR MEASURING MRE11 IN TISSUES TO PREDICT CYSTECTOMY OR BLADDER SPARING SURGERY PLUS CHEMORADIATION THERAPY

(71) Applicant: H. Lee Moffitt Cancer Center and Research Institute, Inc., Tampa, FL (US)

(72) Inventor: Anthony M. Magliocco, Orlando, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 365 days.

(21) Appl. No.: 16/534,111

(22) Filed: Aug. 7, 2019

(65) Prior Publication Data

US 2019/0391153 A1 Dec. 26, 2019

Related U.S. Application Data

(63) Continuation of application No. PCT/US2018/017780, filed on Feb. 12, 2018.

(60) Provisional application No. 62/571,694, filed on Oct. 12, 2017, provisional application No. 62/457,333, filed on Feb. 10, 2017.

(51) Int. Cl.
*G01N 33/574* (2006.01)
*A61N 5/00* (2006.01)
*A61N 5/10* (2006.01)

(52) U.S. Cl.
CPC . *G01N 33/57496* (2013.01); *G01N 33/57407* (2013.01); *A61N 5/10* (2013.01); *A61N 2005/1098* (2013.01)

(58) Field of Classification Search
CPC ....... G01N 33/57496; G01N 33/57407; G01N 2800/52
See application file for complete search history.

(56) References Cited

U.S. PATENT DOCUMENTS

2015/0313922 A1  11/2015  Petrini et al.

OTHER PUBLICATIONS

International Search Report and Written Opinion issued by the International Searching Authority dated Feb. 12, 2018 for international priority application No. PCT/US18/17780.
International Preliminary Report on Patentability issued by the International Bureau dated Aug. 22, 2019 for international priority application No. PCT/US18/17780.
Zhu, Wei-Guo et al. Translocation of MRE11 from the Nucleus to the Cytoplasm as a Mechanism of Radiosensitization by Heat. Radiation Research (2001) 156, 95-102.
Choudhury, A. et al. MRE11 expression is predictive of cause-specific survival following radical radiotherapy for muscle invasive bladder cancer. Cancer Res. Sep. 15, 2010; 70(18): 7017-7026.
Mirza, A. and A. Choudhury. Bladder Preservation for Muscle Invasive Bladder Cancer. Bladder Cancer 2 (2016) 151-163.

*Primary Examiner* — Mark Halvorson
(74) *Attorney, Agent, or Firm* — Michele L. Lawson; Smith & Hopen, P.A.

(57) ABSTRACT

A method of identifying cancer patients who would be responsive to bladder sparing surgery plus chemoradiation therapy or cystectomy using expression of MRE11 in a nuclear to cytoplasmic ratio is presented.

11 Claims, 33 Drawing Sheets

AQUA = Average target pixel intensity/Area of the defined compartment

Figure 2A-G

Status of Patients from ALL MRE11 Data Received

| | # Patients |
|---|---|
| Tested for MRE11 | 308 |
| - Normal controls | -11 |
| - Failed cores | -45 |
| - Non-invasive carcinomas | -74 |
| - Ineligible | -10 |
| Analyzable and eligible for MRE11 | 168 |
| With H-Score data | 158 |
| With Percent Positive Nuclei data | 158 |
| With Nuclear/Cytoplasmic Ratio data | 135 |
| With All Three of the Above | 125 |

FIG. 3

Table 1.3
Patients used in MRE11 Nuclear/Cytoplasmic Ratio Analysis

| | # Patients |
|---|---|
| Analyzable patients from 8802/8903/9506/9706/9906/0233 | 465 |
| Not Analyzable and eligible for MRE11 | 330 |
| *Analyzable and eligible for MRE11 Nuclear/Cytoplasmic Ratio* | *135* |

FIG. 4

Characteristics of Patients by MRE11 AQUA N/C Ratio

| | ≤ Q1 (n=34) n (%) | > Q1 (n=101) n (%) | p-value* |
|---|---|---|---|
| Age (years) | | | 0.62 |
| <70 | 22 (65) | 70 (69) | |
| ≥70 | 12 (35) | 31 (31) | |
| Zubrod | | | 0.038 |
| 0 | 34 (100) | 88 (87) | |
| 1 | 0 (0) | 13 (13) | |
| Gender | | | 0.59 |
| Male | 29 (85) | 82 (81) | |
| Female | 5 (15) | 19 (19) | |
| Race | | | 0.65 |
| White | 23 (68) | 64 (63) | |
| Other | 11 (32) | 37 (37) | |
| Histology | | | 0.57 |
| Transitional | 34 (100) | 97 (96) | |
| Other | 0 (0) | 4 (4) | |
| T-Stage | | | 0.39 |
| T2 | 23 (68) | 76 (75) | |
| T3-T4 | 11 (32) | 25 (25) | |

Characteristics of Patients by MRE11 Nuclear to Cytoplasmic Ratio (Lower Quartile)
(n=135)

|  | ≤Q1 (n=34) | >Q1 (n=101) | p-value* |
|---|---|---|---|
| Age (years) | | | |
| Median | 64.5 | 65 | |
| Min - Max | 36 - 79 | 34 - 90 | |
| Age (years) | | | 0.62 |
| <70 | 22 ( 64.7%) | 70 ( 69.3%) | |
| ≥70 | 12 ( 35.3%) | 31 ( 30.7%) | |
| Zubrod | | | 0.038 |
| 0 | 34 (100.0%) | 88 ( 87.1%) | |
| 1 | 0 ( 0.0%) | 13 ( 12.9%) | |
| Gender | | | 0.59 |
| Male | 29 ( 85.3%) | 82 ( 81.2%) | |
| Female | 5 ( 14.7%) | 19 ( 18.8%) | |
| Race | | | 0.65 |
| White | 23 ( 67.6%) | 64 ( 63.4%) | |
| Other | 11 ( 32.4%) | 37 ( 36.6%) | |
| Histology | | | 0.57 |
| Transitional | 34 (100.0%) | 97 ( 96.0%) | |
| Other | 0 ( 0.0%) | 4 ( 4.0%) | |
| T-Stage | | | 0.39 |
| T2 | 23 ( 67.6%) | 76 ( 75.2%) | |
| T3-T4 | 11 ( 32.4%) | 25 ( 24.8%) | |

*p-value from Chi-square or Fisher's Exact Test

FIG. 7

Follow-Up Summary by MRE11 Nuclear to Cytoplasmic Ratio (Lower Quartile)
(n=135)

| | ≤Q1 | >Q1 | Total |
|---|---|---|---|
| | n=34 | n=101 | n=135 |
| Median (min-max) follow-up for all patients (years) | 2.86 (0.26-16.49) | 4.02 (0.11-11.65) | 3.73 (0.11-16.49) |
| | n=15 | n=51 | n=66 |
| Median (min-max) follow-up for surviving (years) | 3.63 (2.02-10.79) | 5.01 (0.55-11.65) | 4.98 (0.55-11.65) |

FIG. 8

| | SOC (n=34) n (%) | DX (n=101) n (%) | Total (n=135) n (%) |
|---|---|---|---|
| Complete Response* | | | |
| Yes | 20 (63) | 67 (69) | 87 (67) |
| No | 12 (38) | 30 (31) | 42 (33) |
| Overall Survival | | | |
| Alive | 15 (44) | 51 (50) | 66 (49) |
| Dead | 19 (56) | 50 (50) | 69 (51) |
| Disease-Specific Mortality | | | |
| Alive | 15 (44) | 51 (50) | 66 (49) |
| Dead from Bladder Cancer | 15 (44) | 27 (27) | 42 (31) |
| Dead from Non-Bladder Cancer | 4 (12) | 23 (23) | 27 (20) |
| Bladder Intact Survival | | | |
| Alive/Bladder Intact | 15 (44) | 46 (46) | 61 (45) |
| Dead or Cystectomy | 19 (56) | 55 (54) | 74 (55) |

FIG. 9

2 and 4-Year Estimated Outcome Rates by MRE11 Nuclear to Cytoplasmic Ratio (Lower Quartile) (n=135)

| | OS | | DSF | | Bladder Intact OS | |
|---|---|---|---|---|---|---|
| | 2y-% (95% CI) | 4y-% (95% CI) | 2y-% (95% CI) | 4y-% (95% CI) | 2y-% (95% CI) | 4y-% (95% CI) |
| ≤Q1 | 71 (52,83) | 51 (32,68) | 26 (13,42) | 41 (23,58) | 65 (46,78) | 49 (30,66) |
| >Q1 | 78 (68,85) | 64 (54,73) | 12 (7,19) | 21 (13,30) | 71 (61,79) | 59 (48,68) |
| p-value | 0.52* | | 0.033† | | 0.79* | |

*Log-rank p-value; †Gray's test p-value

FIG. 10

Univariate Cox Proportional Hazards Models for MRE11 Nuclear to Cytoplasmic Ratio (Lower Quartile) (n=135)

| Endpoint | MRE11 | Hazard Ratio | 95% C.I. LL | 95% C.I. UL | p-value |
|---|---|---|---|---|---|
| OS | ≤Q1 | 1.00 | -- | -- | -- |
|  | >Q1 | 0.84 | 0.488 | 1.44 | 0.52* |
| DSF | ≤Q1 | 1.00 | -- | -- | -- |
|  | >Q1 | 0.50 | 0.26 | 0.93 | 0.03† |
| Bladder Intact OS | ≤Q1 | 1.00 | -- | -- | -- |
|  | >Q1 | 0.93 | 0.545 | 1.59 | 0.79† |

*p-value from Chi-square test using the Cox proportional hazards model.
†p-value from Fine-Gray regression model

FIG. 14

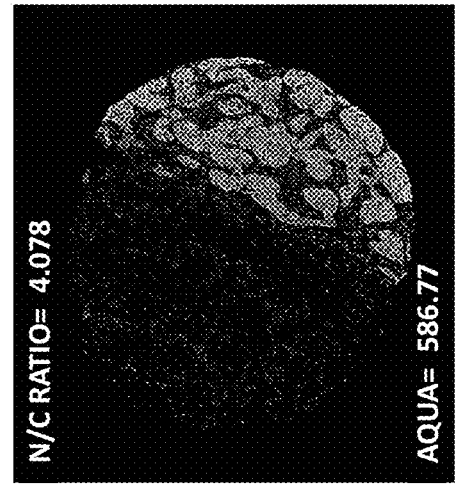
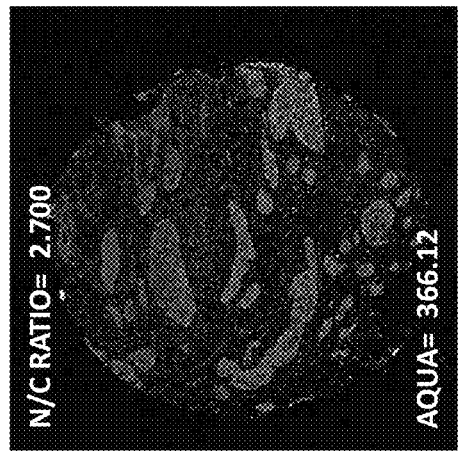
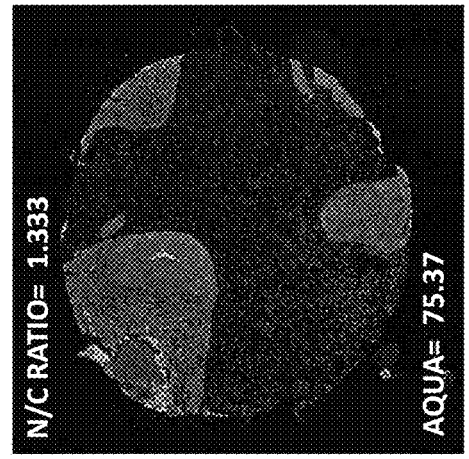
FIG. 18

Prior Art: Choudhury, A. et al., Cancer Research 70:7017-26, 2010

MRE11 FUNCTION

Prior art: Choudhuty, A. et al., Cancer Research 70: 7017-26, 2010

Prior art: Choudhuty, A. et al., Cancer Research 70: 7017-26, 2010

MRE11 AQUA N/C Ratio Removes Batch Effect

MRE11 Nuclear AQUA

MRE11 AQUA N/C Ratio Removes Batch Effect

MRE11 Cytoplasmic AQUA

Characteristics of Analyzable vs. Non-Analyzable Patients for MRE11

| | Non Analyzable (n=330) n (%) | Analyzable (n=135) n (%) | p-value |
|---|---|---|---|
| Age (years) | | | 0.27 |
| <70 | 207 (63) | 92 (68) | |
| ≥70 | 123 (37) | 43 (32) | |
| Zubrod | | | 0.68 |
| 0 | 294 (89) | 122 (90) | |
| 1 | 36 (11) | 13 (10) | |
| Gender | | | 0.90 |
| Male | 273 (83) | 111 (82) | |
| Female | 57 (17) | 24 (18) | |
| Race | | | 0.0001 |
| White | 268 (81) | 87 (64) | |
| Other | 62 (19) | 48 (36) | |
| Histology | | | 0.094 |
| Transitional | 307 (93) | 131 (97) | |
| Other | 23 (7) | 4 (3) | |
| T-Stage | | | 0.0003 |
| T2 | 182 (55) | 99 (73) | |
| T3-T4 | 148 (45) | 36 (27) | |

FIG. 24

METHOD FOR MEASURING MRE11 IN TISSUES TO PREDICT CYSTECTOMY OR BLADDER SPARING SURGERY PLUS CHEMORADIATION THERAPY

CROSS REFERENCE TO RELATED APPLICATIONS

This application is a continuation of and claims priority to International Patent Application No. PCT/US2018/017780, filed Feb. 12, 2018, which claims priority to U.S. Provisional Patent Application No. 62/571,694, entitled "Method for Measuring MRE11 in Tissues to Predict Chemoradiation Response Using Immunohistochemistry and Digital Imaging", filed on Oct. 12, 2017, and U.S. Provisional Patent Application No. 62/457,333, entitled "Method for Measuring MRE11 in Tissues to Predict Chemoradiation Response Using AQUA and Digital Imaging", filed on Feb. 10, 2017, the contents of each of which are herein incorporated by reference.

GOVERNMENTAL SUPPORT

This invention was made with Government support under Grant Nos. U10CA180868; U10CA180822; UG1CA189867; and U24CA196067 awarded by the National Institutes of Health. The Government has certain rights in the invention.

FIELD OF INVENTION

This invention relates to tumorigenic assays. Specifically, the invention provides a method of predicting a treatment course for bladder cancer patients based on levels of MRE11.

BACKGROUND OF THE INVENTION

Biomarkers are needed to help select patients with muscle invading bladder cancer (MIBC) for bladder sparing chemotherapy and chemoradiation treatment (CRT). Higher MRE11 expression has been identified as a potential RT response marker in MIBC. MRE11 protein is involved in the DNA double strand break repair mechanism. Previous work has indicated MRE11 protein measurement may identify patients who are resistant to radical radiotherapy.

There are several challenges to MRE11 measurement. There is currently no standardized assay for MRE11 protein measurement based on quantitative IHC. The publications used quartile measurements and proprietary approaches making the methods not duplicable as there are no samples available. Any new method must be Clinical Laboratory Improvement Amendment (CLIA) eligible. Case material specimens in TMAs, slides and blocks all have a risk of batch effect.

Accordingly, what is needed is to develop and validate a new assay for MRE11 measurement that is suitable for use in future clinical trials which allows for normalization of signal using internal control ratio of nucleus/cytoplasm ratio.

SUMMARY OF INVENTION

The inventors have evaluated associations between MRE11 expression and outcome in patients from 6 NRG/RTOG bladder-sparing RT protocols. Archival tissue via TMA or unstained slides was used. Cases were stained with anti MRE11 antibody Rabbit mAb, clone EPR3471 (Epitomics at 1:1500 dilution). Slides were scanned on an Aperio FL instrument and analyzed via Automated Quantitative Image analysis (AQUA). MRE11 scores were determined within the nucleus and cytoplasm of urothelial cells and a ratio of nuclear to cytoplasmic (N/C) score calculated. A ratio was used to normalize scores and overcome pre-analytical variation.

MRE11 N/C was analyzed by quartile cut points. Cumulative incidence was used to estimate disease-specific mortality (DSM; failure=bladder cancer death) and Fine-Gray models were used to evaluate associations between MRE11 and DSM. Cox models were used for overall survival (OS; death) and bladder-intact survival (BIS; cystectomy/death).

Out of 465 eligible patients, tissue was available and MRE11 N/C determined for 135. Analyzable patients were less likely to be white (p=0.0001) and more likely to be T2 (p=0.0003).

Median MRE11 N/C was 2.41 (min-max: 0.69-6.03). Patients with MRE11 N/C≤1.49 (lower quartile) were associated with significantly higher DSM (HR=2, 95% CI: 1.1, 3.8, p=0.03). The 4-year DSM was 41% for patients with MER11 N/C≤1.49 vs. 21% for patients with MER11 N/C was >1.49. MRE11 N/C was not associated with OS or BIS.

AQUA analysis allows precise measurement of this marker in tissue samples. Low expression of MRE11 N/C (≤1.49) is associated with significantly higher DSM. This adds further evidence of MRE11 as a potential RT response biomarker for selection of patients most likely to respond to bladder-sparing chemoradiation therapy.

In an embodiment, a method of determining therapy for a cancer patient based on expression of MRE11 is presented comprising: obtaining a sample from the patient; determining in the sample an expression level of MRE11 wherein the determining step comprises: contacting the sample with an antibody that recognizes MRE11 protein in an immunoassay; detecting the complex between the antibody and the MRE11 protein; determining a total MRE11 score using immunohistochemistry wherein the total MRE11 score is based on ratio between presence of MRE11 in nucleus versus cytoplasm of cell; and administering aggressive therapy to the patient if the total MRE11 score is below a calculated lower quartile. A multiplex system may be used for the immunohistochemistry. The sample may be measured by cytopathology, urine cytology, or circulating tumor cell test.

The cancer can be selected from the group consisting of bladder cancer, breast cancer, oral cancer, laryngeal cancer, prostate cancer, liver cancer, pancreatic cancer, skin cancer, renal cancer, colon cancer, uterine cancer, brain cancer, ovarian cancer, endometrial cancer, lung cancer, head and neck cancer, cervical cancer, sarcoma, neuroendocrine tumors, and gastrointestinal cancers.

In some embodiments, the cancer is bladder cancer, in some cases muscle-invasive bladder cancer and the aggressive therapy is cystectomy which is administered if the cut point for the calculated lower quartile is equal to or below 1.49. A total MRE11 score below this cut point allows the patient to avoid bladder sparing surgery plus chemoradiation therapy.

In an embodiment, a method of predicting therapy response and treating a patient having bladder cancer based on MRE11 expression is presented comprising: obtaining a sample from the patient; determining in the sample an expression level of MRE11 wherein the determining step comprises: contacting the sample with an antibody that recognizes MRE11 protein in an immunoassay; detecting the complex between the antibody and the MRE11 protein; determining a total MRE11 score using immunohistochemistry wherein the total MRE11 score is based on ratio between presence of MRE11 in nucleus versus cytoplasm of cell; and administering bladder sparing surgery plus chemoradiation therapy to the patient if the total MRE11 score is above a cut point for a calculated lower quartile.

In some embodiments, the bladder cancer is muscle-invasive bladder cancer and the cut point for the calculated lower quartile is above 1.49. The sample may be measured by cytopathology, urine cytology, or circulating tumor cell test.

The method of claim 10, wherein the immunohistochemistry used is a multiplex system.

The method of claim 10, wherein the bladder cancer is muscle-invasive bladder cancer.

In an embodiment, a method of predicting the overall survival prognosis of a patient having bladder cancer, such as muscle-invasive bladder cancer, is presented comprising: obtaining a tissue sample from the patient; determining in the tissue sample an expression level of MRE11 wherein the determining step comprises: contacting the sample with an antibody that recognizes MRE11 protein in an immunoassay; detecting the complex between the antibody and the MRE11 protein; determining a nuclear MRE11 score for presence of MRE11 in nucleus of a cell using immunohistochemistry; determining a cytoplasmic MRE11 score for presence of MRE11 in cytoplasm of the cell using immunohistochemistry; determining a total MRE11 score wherein the total MRE11 score is based on ratio between the nuclear MRE11 score and the cytoplasmic MRE11 score wherein a total MRE11 score below 1.49 is indicative of a poor prognosis; and administering cystectomy to the patient if the total MRE11 score is equal to or below 1.49. The immunohistochemistry used can be a multiplex system.

BRIEF DESCRIPTION OF THE DRAWINGS

For a fuller understanding of the invention, reference should be made to the following detailed description, taken about the accompanying drawings, in which:

FIG. 3 is a table depicting the status of patients from all MRE11 data received.

FIG. 4 is a table depicting a list of the clinical trials from which material was obtained for the MRE11 nuclear/cytoplasmic ratio analysis (n=135).

FIG. 5 is a table depicting the characteristics of patients by MRE11 AQUA N/C Ratio.

FIG. 7 is a table depicting the characteristics of patients by MRE11 nuclear to cytoplasmic ratio (Lower quartile) (n=135). The table depicts the results of the analysis of patient characteristics between cases with low MRE11 NC ratio vs high MRE11 NC ratio. There is no difference except for Zubrod Score where high ratio had greater chance of score 1 (with symptoms vs no symptoms).

FIG. 8 is a table depicting the follow-up summary by MRE11 nuclear to cytoplasmic ratio (Lower quartile) (n=135). The median follow-up time for patients with low and high MRE11 is shown as well as the total MRE11 scores.

FIG. 9 is a table depicting events by MRE11 nuclear to cytoplasmic ratio (Lower quartile) (n=135). The table summarizes the clinical events broken down by MRE11 analysis category (low vs. high).

FIG. 10 is a table depicting the 2 and 4-year outcome rates by MRE11 nuclear to cytoplasmic ratio (Lower quartile) (n=135). The table depicts the outcomes in cases with low and high MRE11 expression as overall survival (OS) and disease specific survival (DSF). Bladder intact is the subset of patients with intact bladders. DSF is significantly ($p<0.03$) lower in low MRE11 expressing tumors.

FIG. 14 is a table depicting univariate Cox proportional hazards models for MRE11 nuclear to cytoplasmic ratio (Lower quartile) (n=135). Cases with High expression show reduced risk of death (OS) and reduced risk of progression. DSF also Reduced risk of death in bladder intact. Only the DSF reaches statistical significance in this analysis.

FIG. 18 is a series of images depicting representative images of invasive bladder cancer TMA cores following immunofluorescence staining for MRE11. TMA cores were stained with DAPI (blue), pan cytokeratin (green), and MRE11 (red). An analysis algorithm was constructed to calculate the nuclear and cytoplasmic AQUA scores using pan cytokeratin (PCK) as the tumor mask. The AQUA score is defined as the average concentration of Cy5 (MRE11) pixel intensity within the tumor area of each TMA core.

FIG. 24 is a table of the characteristics of analyzable versus non-analyzable patients for MRE11.

DETAILED DESCRIPTION OF THE PREFERRED EMBODIMENT

Figure 1:
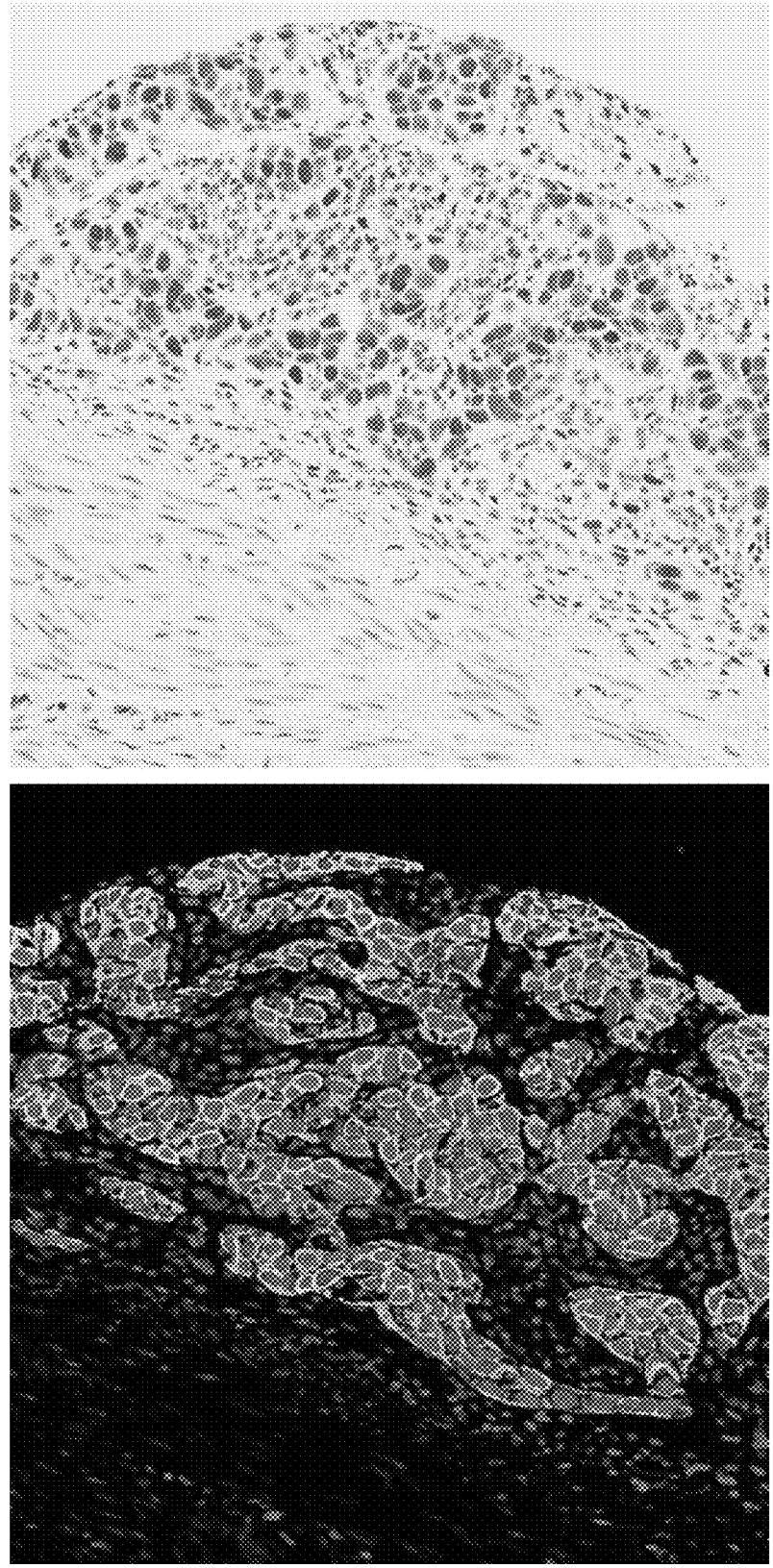
FIG. 1 is an image of MRE stains. Left panel composite image of invasive bladder cancer stained with anti-MRE11 (red) anti-keratin (green) and DAPI which stains nuclei. The same region stained with conventional DAB IHC method against MRE11 is seen in the right panel.
Figure 2:
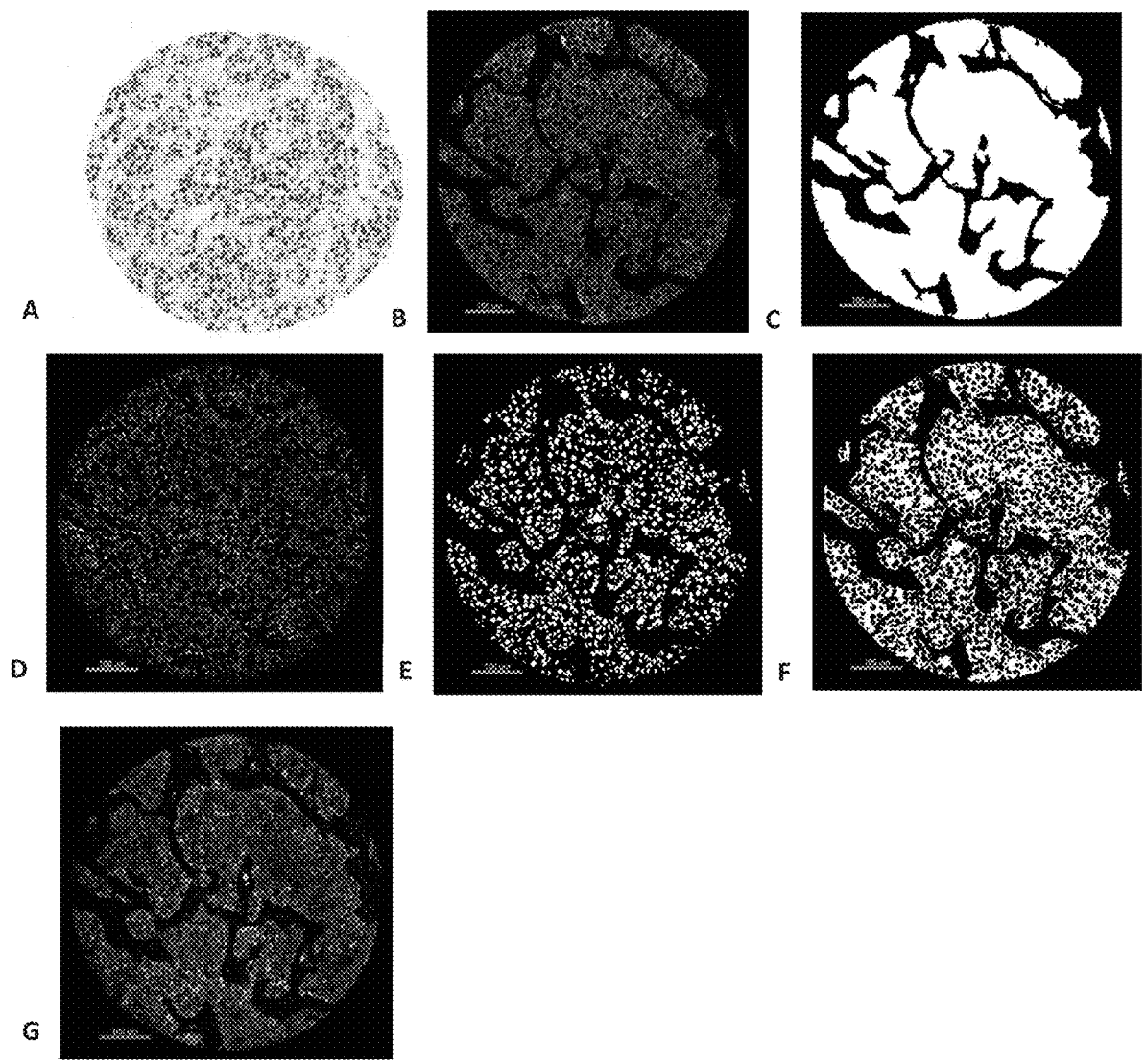
FIG. 2A-G is a series of images depicting an MRE stain showing DAB-IHC vs. IF-IHC. The figures depict each component of the tissue, cytoplasm, nucleus and target. To really understand the benefits of the multiplexing/HistoRx platform over normal, what the inventors call DAB-IHC (DAB being the brown dye that used to identify the biomarkers), the inventors present an example of how a tissue is analyzed by DAB-IHC and using the digital multiplexing/ HistoRx platform. The images show a piece of tumour tissue stained for a nuclear biomarker like ER. To score the biomarker expression in this tissue one would need to be able to differentiate between tumour cells and non-tumour cells and then judge the intensity and coverage of the staining. (A) regular IHC DAB stain; (B) IF cytokeratin channel; (C) AQUA tumor "mask"—computed area of keratin positive cells; (D) DAPI channel-staining nuclei; (E) AQUA nuclear MASK—area of image containing nuclei within keratin mask; (F) AQUA cytoplasmic MASK— tumor mask with nuclear mask subtracted to reveal area of cytoplasm; (G) MRE channel—signal channel in which the signal intensity is measured within the tumor nuclear mask and the tumor cytoplasmic mask.
Figure 6A:
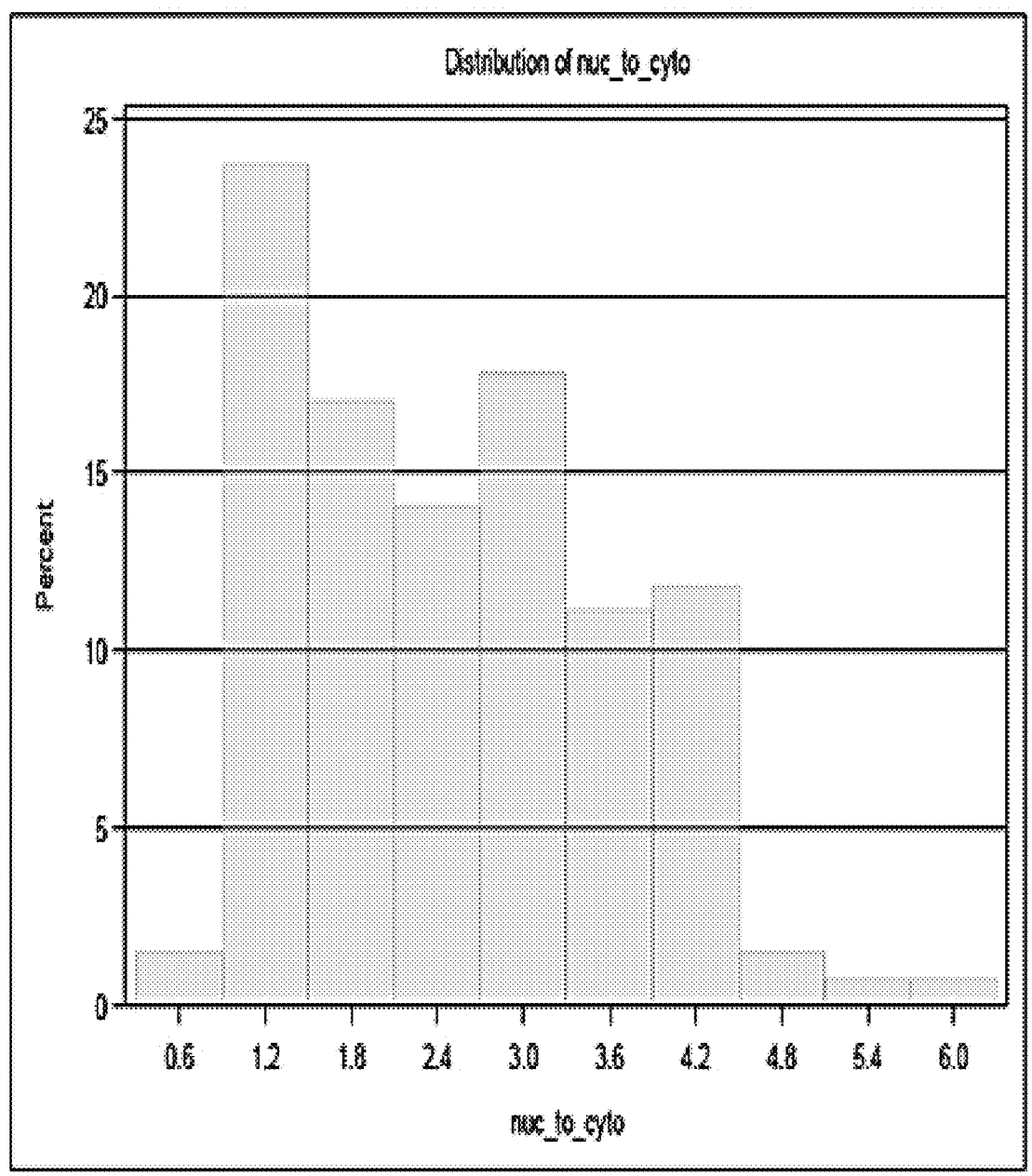
FIG. 6A is a histogram depicting the data distribution for the MRE11 AQUA nuclear/cytoplasmic ratio.
Figure 6B:
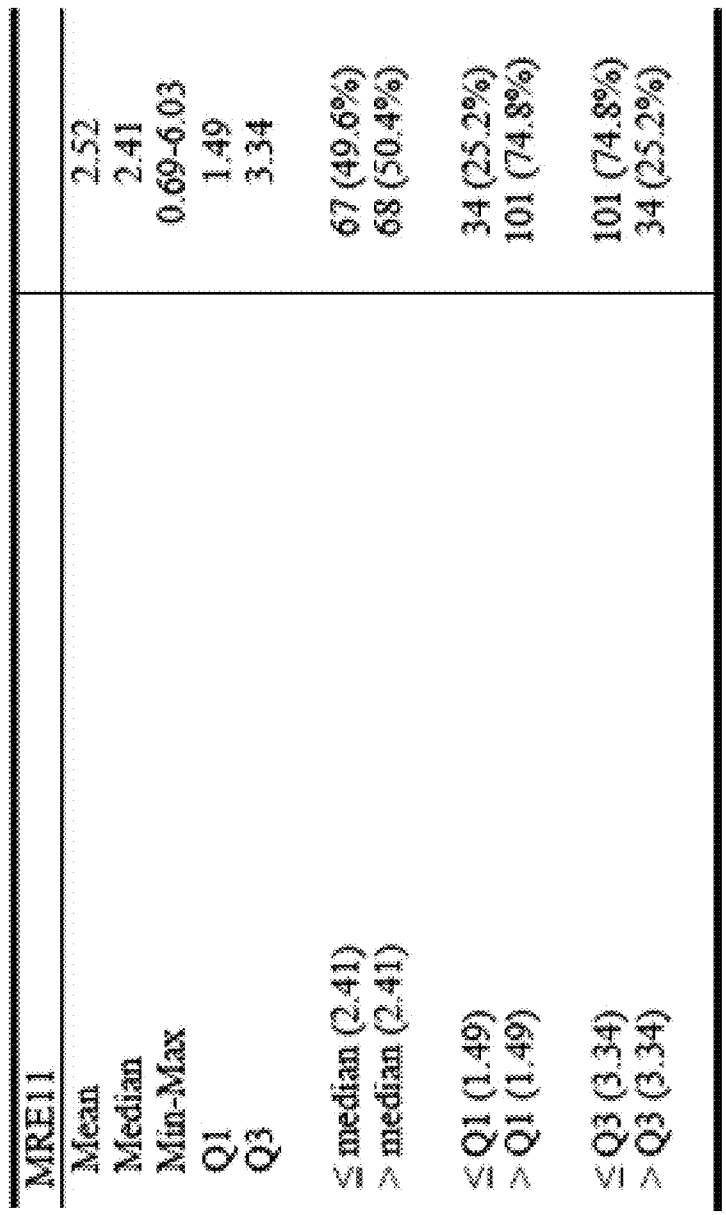
FIG. 6B is a table showing the distribution of MRE11 nuclear/cytoplasmic ratio (n=135). Mean ratio 2.52, median 2.41, lower quartile 1.49.
Figure 11A:
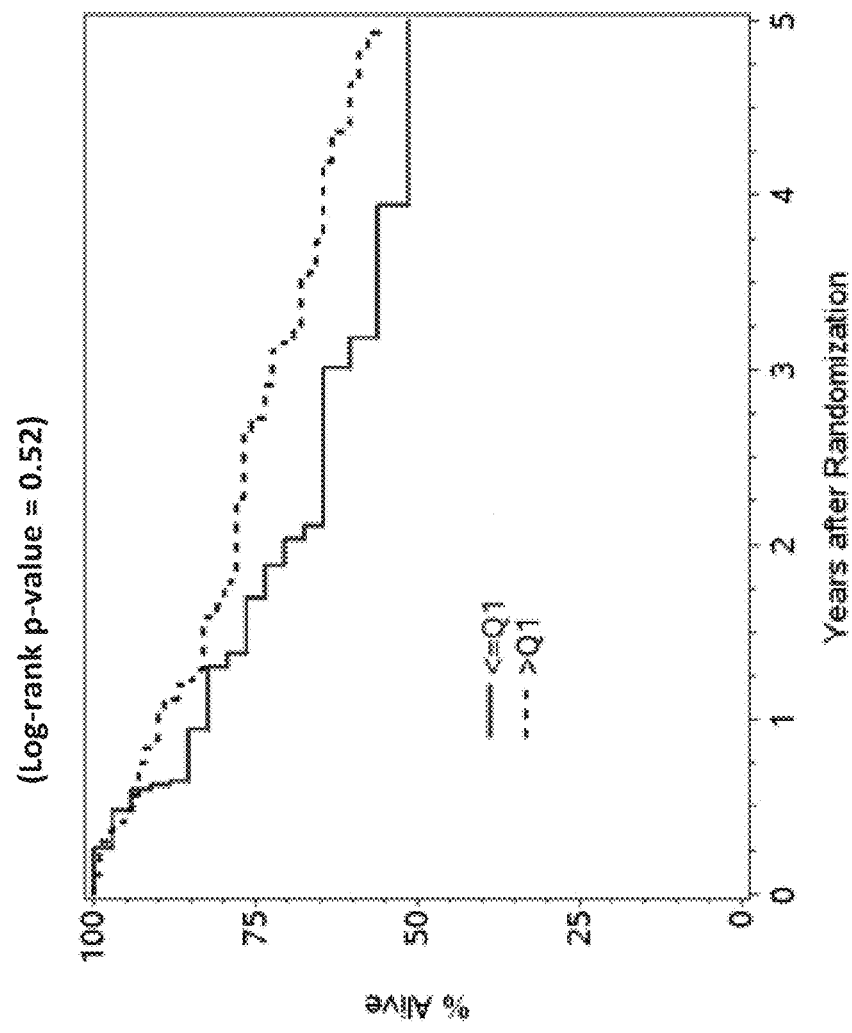
FIG. 11A is an image depicting overall survival (OS) by MRE11 nuclear to cytoplasmic ratio broken down by MRE11 score category (low quartile, median and upper quartile). There is no significant difference but the biggest separation is noted in the group with the lowest quartile expression of MRE11. (A) OS by MRE11 nuclear to cytoplasmic ratio (Lower quartile) log rank p-value=0.52.
Figure 11B:
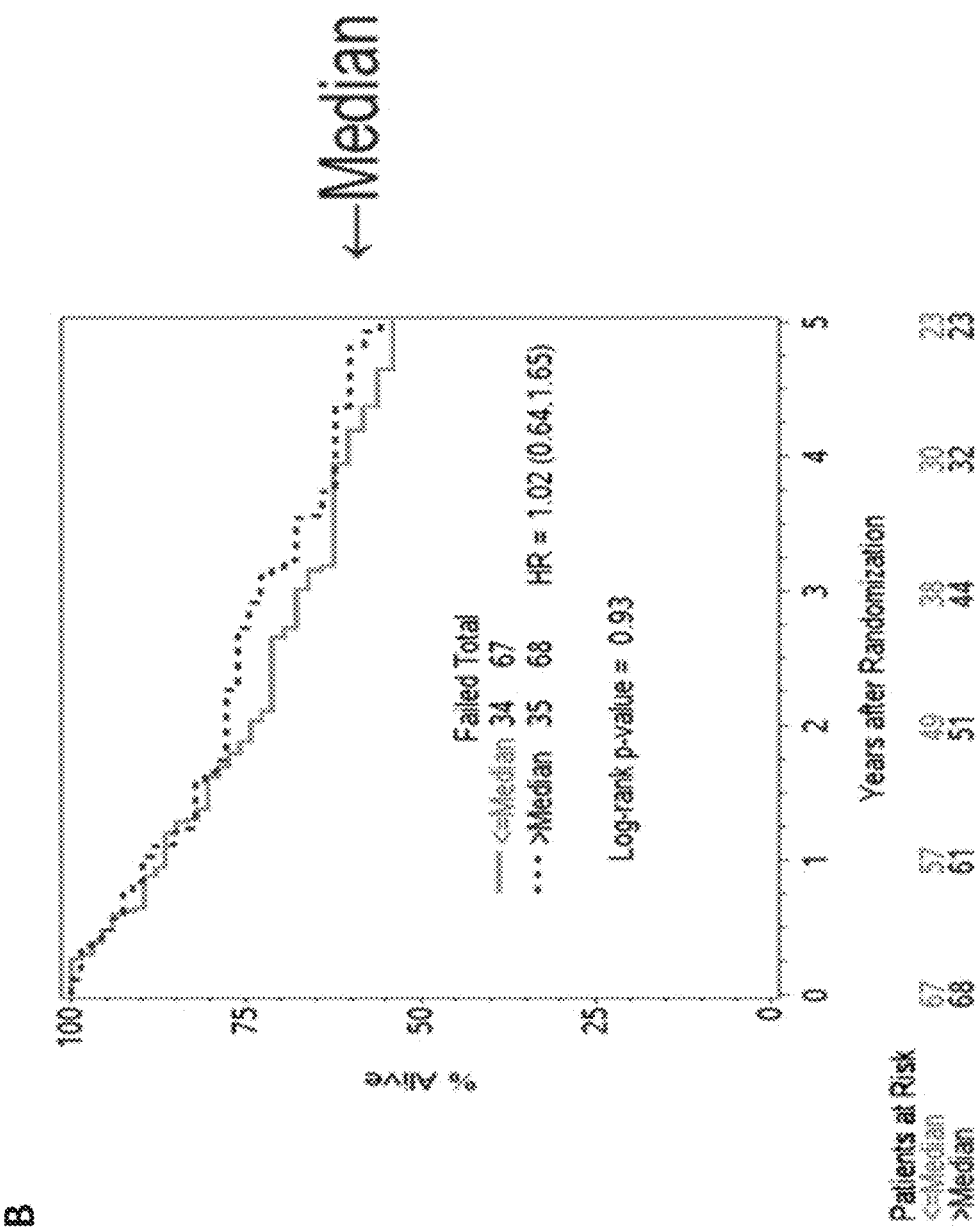
FIG. 11B is an image depicting overall survival (OS) by MRE11 nuclear to cytoplasmic ratio broken down by MRE11 score category (low quartile, median and upper quartile). There is no significant difference but the biggest separation is noted in the group with the lowest quartile expression of MRE11. (B) OS by MRE11 nuclear to cytoplasmic ratio (Median) log rank p-value=0.93.
Figure 11C:
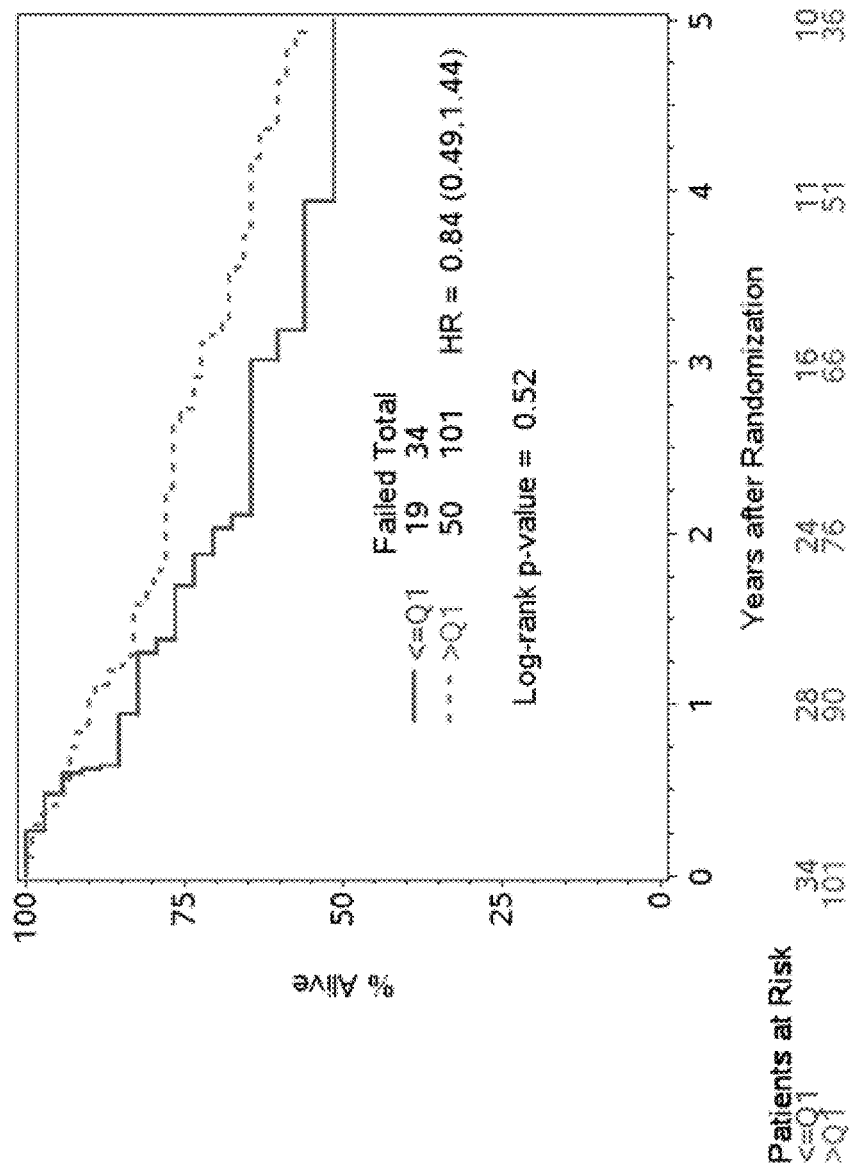
FIG. 11C is an image depicting overall survival (OS) by MRE11 nuclear to cytoplasmic ratio broken down by MRE11 score category (low quartile, median and upper quartile). There is no significant difference but the biggest separation is noted in the group with the lowest quartile expression of MRE11. (C) MRE11 nuclear to cytoplasmic ratio (Lower quartile) log rank p-value=0.52.
Figure 11D:
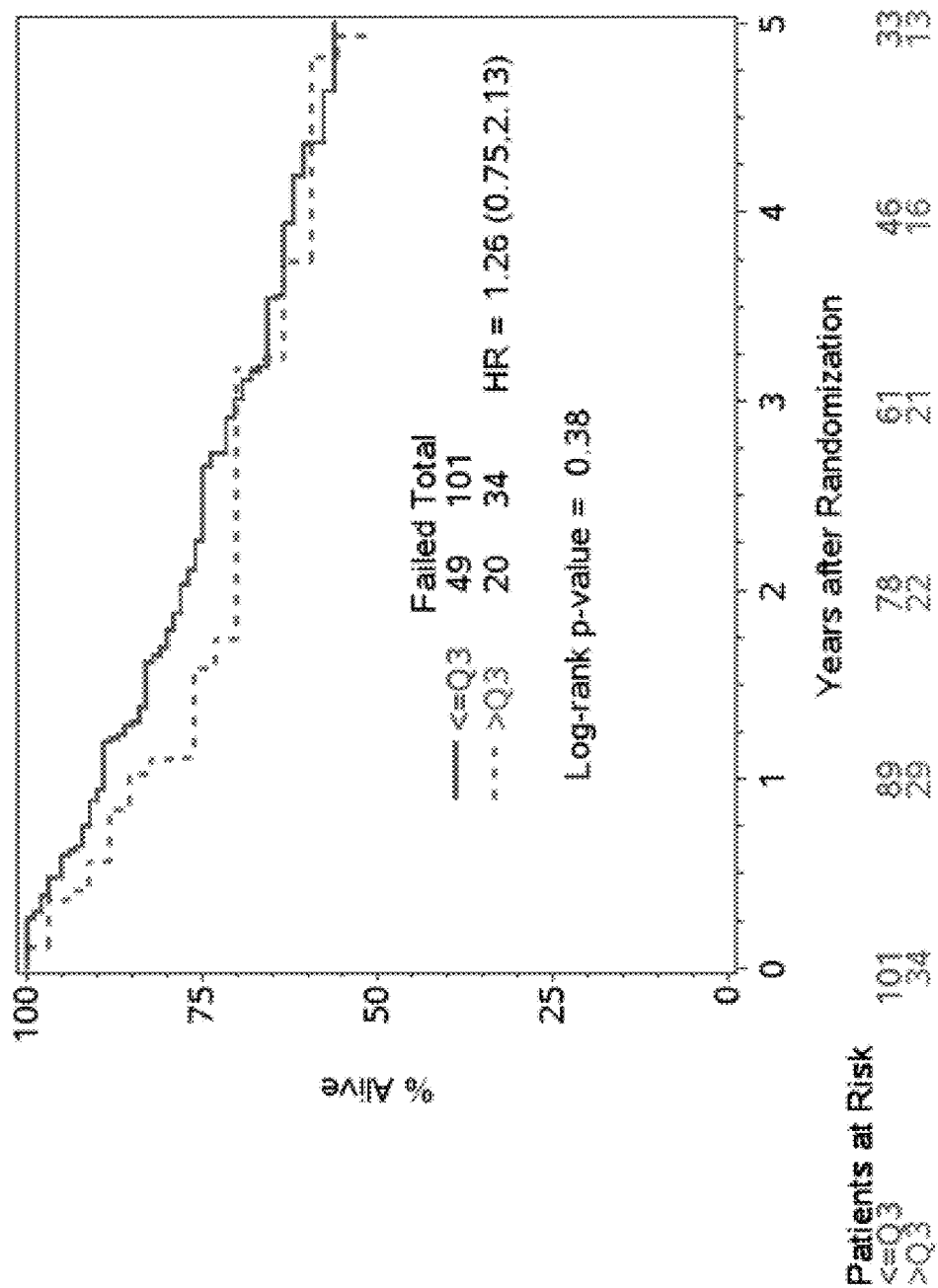
FIG. 11D is an image depicting overall survival (OS) by MRE11 nuclear to cytoplasmic ratio broken down by MRE11 score category (low quartile, median and upper quartile). There is no significant difference but the biggest separation is noted in the group with the lowest quartile expression of MRE11. (D) OS by MRE11 nuclear to cytoplasmic ratio (Upper quartile) log rank p-value=0.38.
Figure 12:
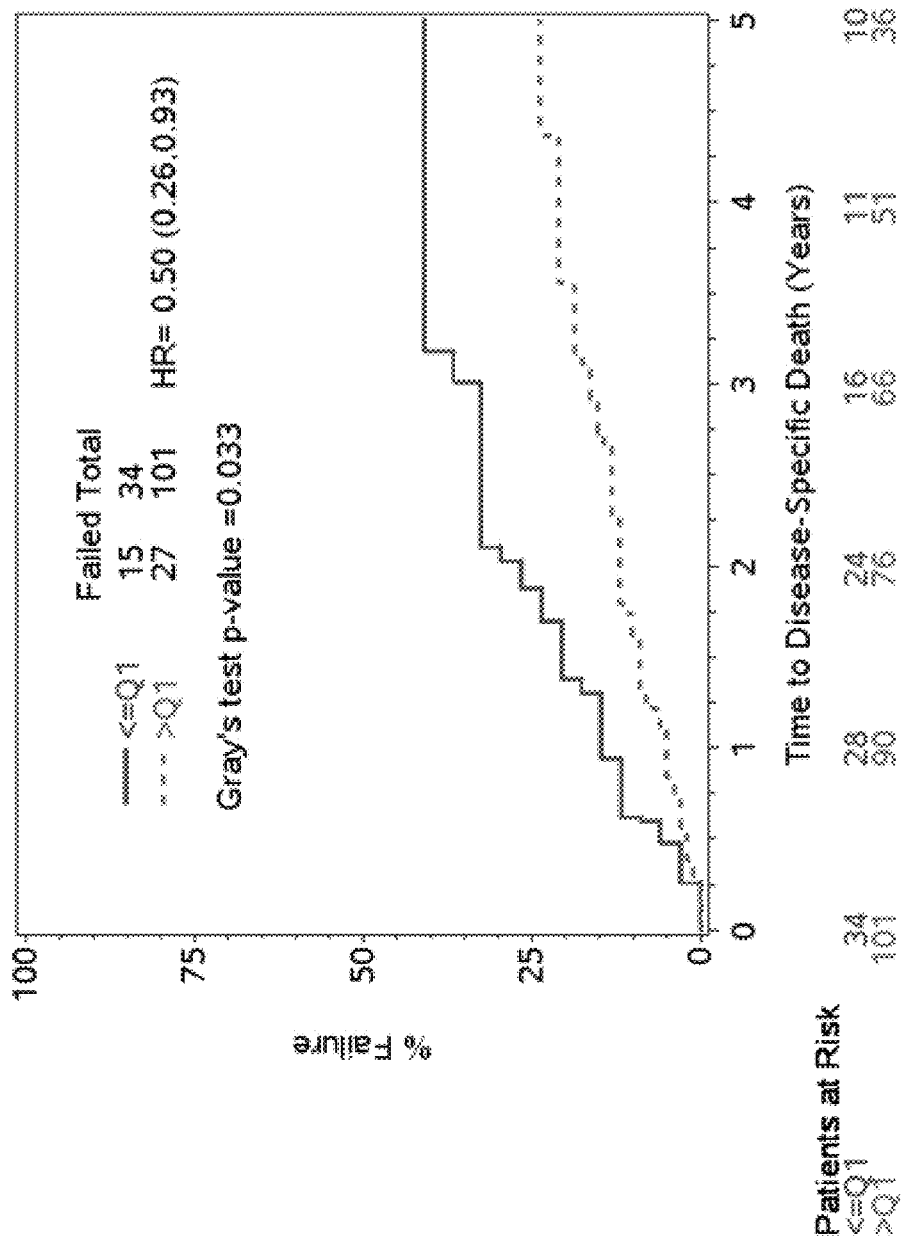
FIG. 12 is an image depicting DSM by MRE11 nuclear to cytoplasmic ratio (Lower quartile) Gray's test p-value=0.033. This image depicts the hazard function. The solid line shows treatment failures in lower quartile of MRE11 expression. The dashed line is the group with greater than lower quartile. The treatment failure rate of low expressors is about double the rate of the higher expressors.
Figure 13:
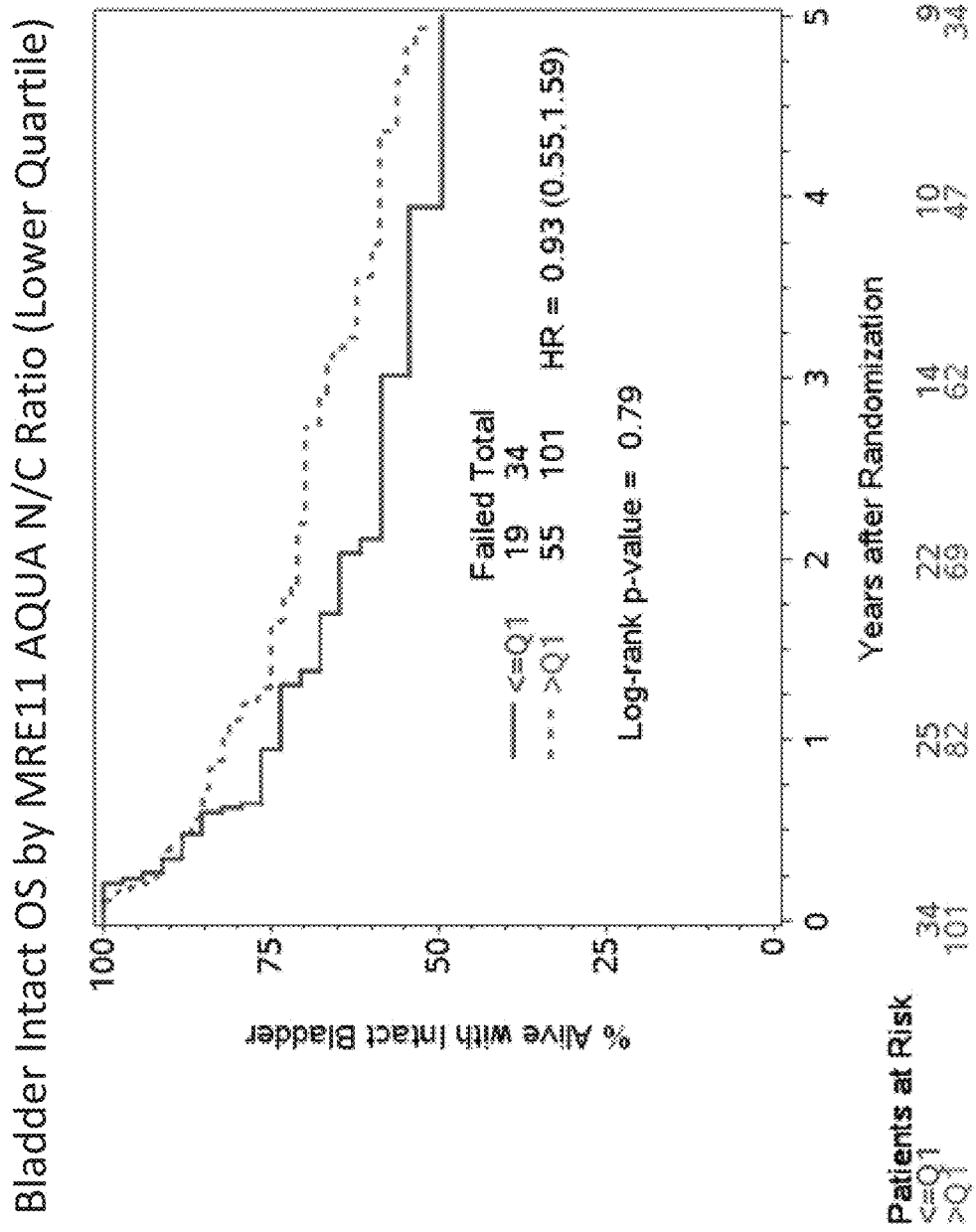
FIG. 13 is an image depicting bladder intact OS by MRE11 nuclear to cytoplasmic ratio (Lower quartile) log rank p-value=0.79. The lower expressors have worse survival but it does not reach statistical significance in this analysis.
Figure 15:
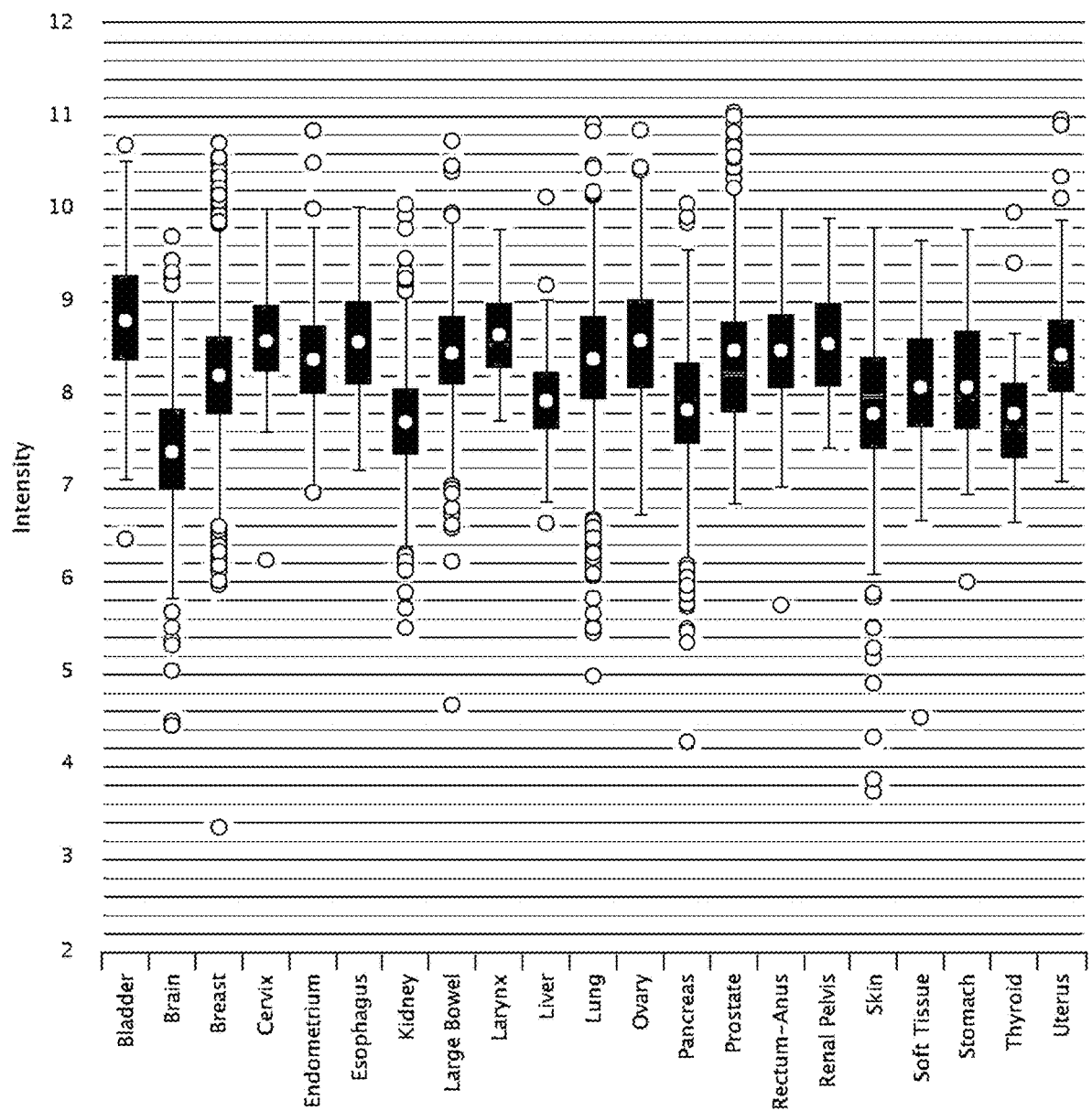
FIG. 15 is an image depicting the analysis of Affymetrix data from Moffitt. The image depicts representation of mRNA expression of MRE11 using Affymetrix gene chip analysis across tumor types. Many tumor types show proportions of cases with low expression (brain, kidney, lung, pancreas, skin) which may indicate that MRE11 can also be useful in these other tumor types to identify cases with resistance to chemoradiation.
Figure 16:
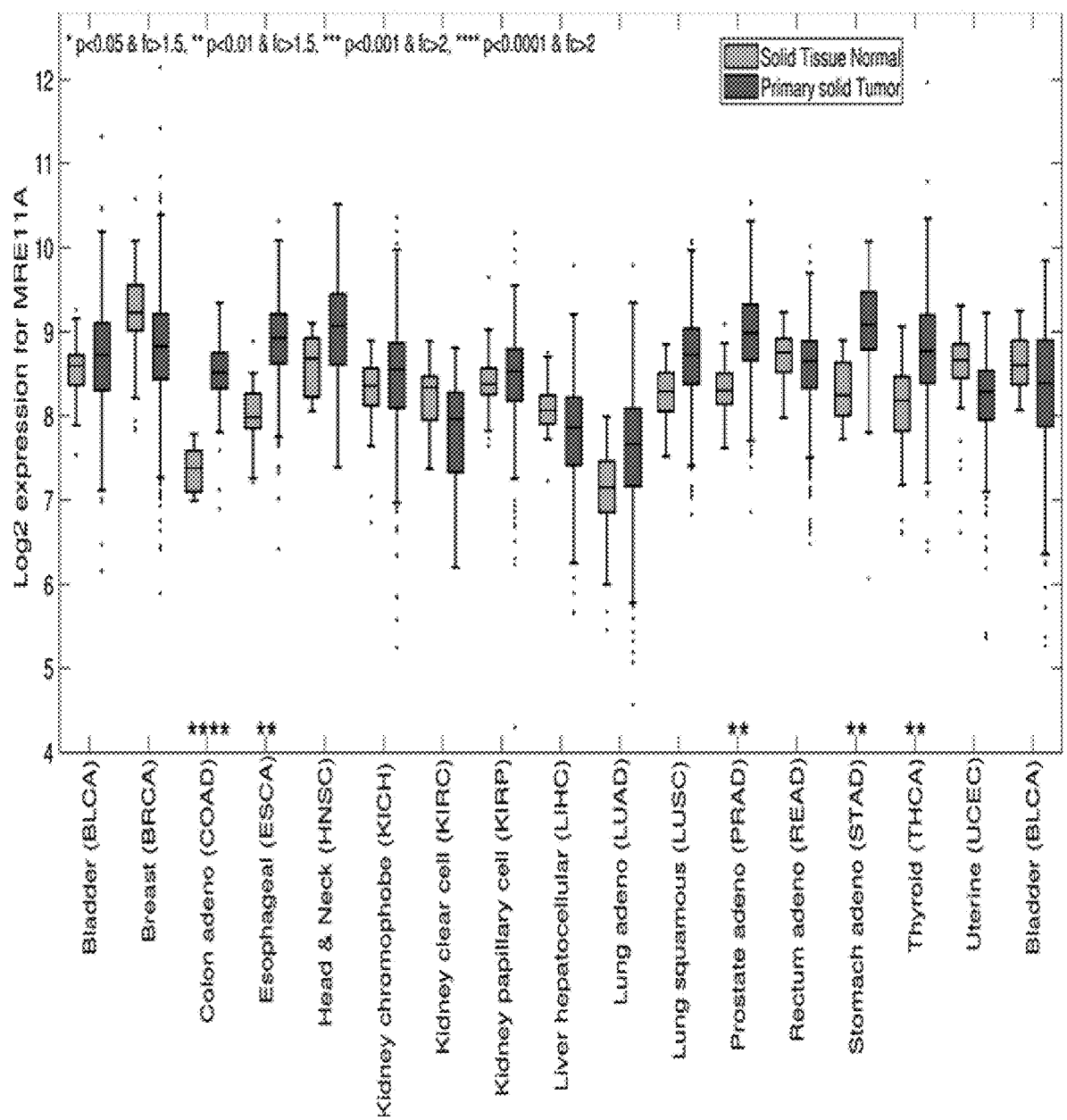
FIG. 16 is an image depicting MRE11 mRNA expression TCGA. This data shows some tumors have differential expression of MRE11 (some also have higher expression) this shows expression in both normal tissue and cancer tissue. Cases with lower expression in cancer include bladder, breast, kidney, uterus.
Figure 17:
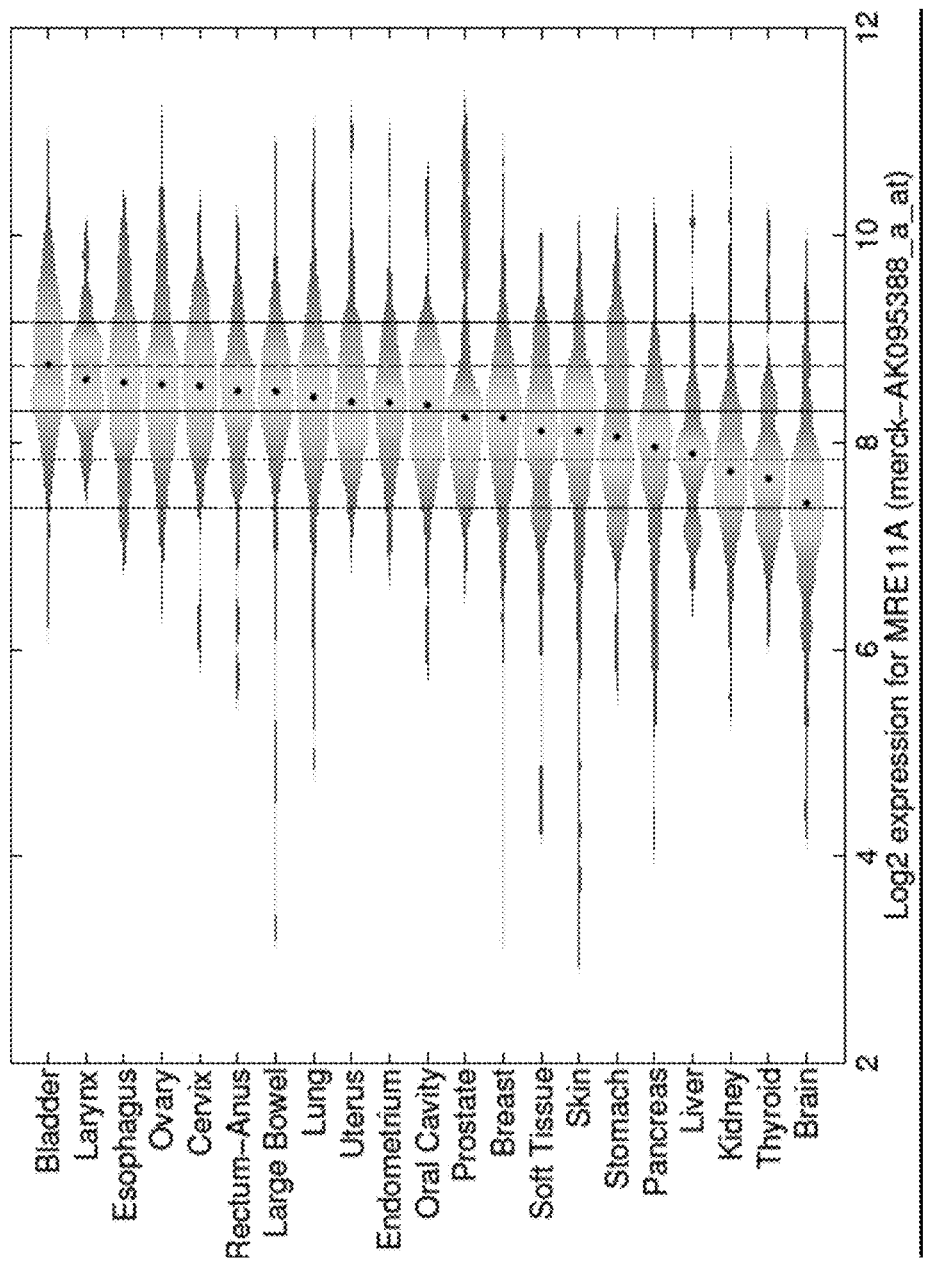
FIG. 17 is an image depicting MRE11 mRNA expression in Moffitt TCC cancers. This figure shows distribution of MRE11 expression across tumor types. Dots represent median shows many tumors have subset of cases with low MRE11 expression, i.e. bladder, large bowel, breast, soft tissue, skin, pancreas, brain, etc.
Figure 19:
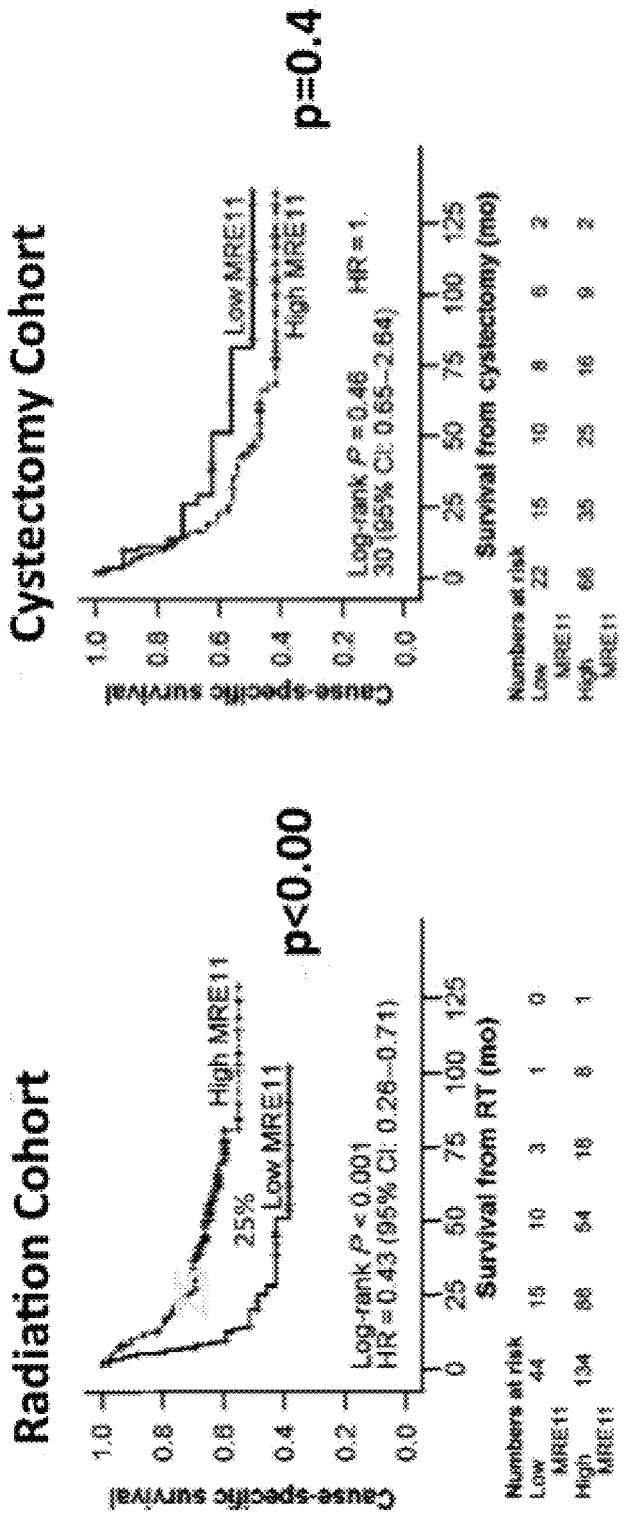
FIG. 19 is a series of prior art images showing that MRE11 protein is predictive of disease-specific survival following XRT but not for cystectomy. In comparison, the inventors have found that patients with low MRE11 expression would be more successfully treated with cystectomy as opposed to a bladder sparing surgery plus chemoradiation.
Figure 20:
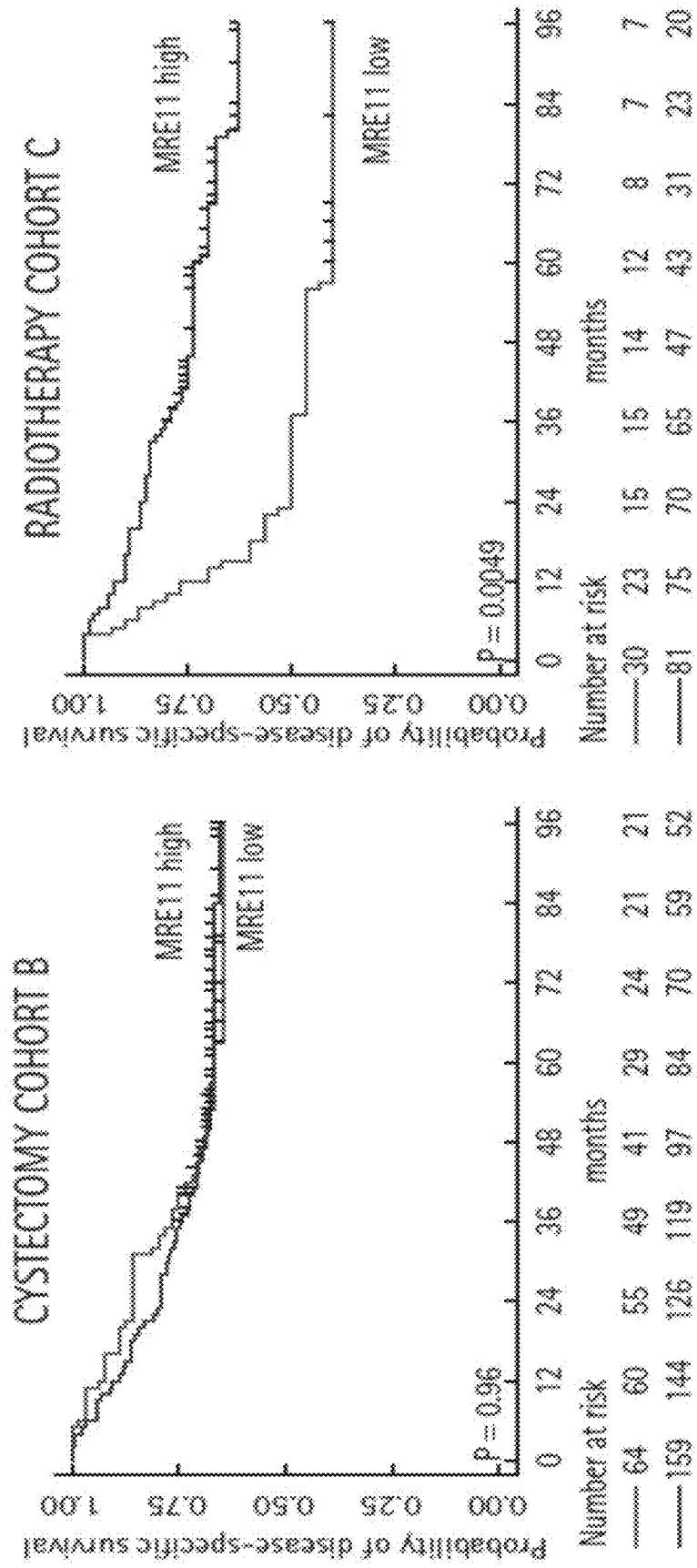
FIG. 20 is a series of prior art images showing that MRE11 protein is predictive of disease-specific survival with ChemoRT but not with cystectomy. In comparison, the inventors have found that patients with low MRE11 expression would be more successfully treated with cystectomy as opposed to a bladder sparing surgery plus chemoradiation.
Figure 21A:
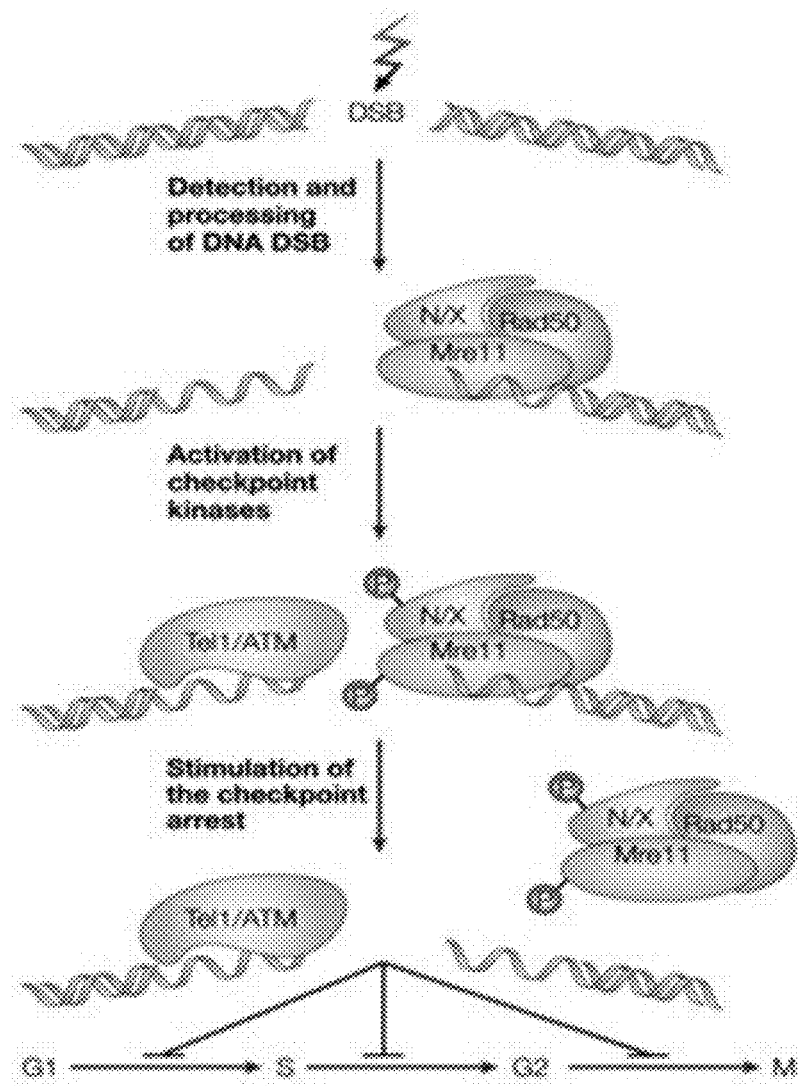
FIG. 21A is a prior art image depicting MRE function. (Choudhuty, A. et al., Cancer Research 70: 7017-26, 2010)
Figure 21B:
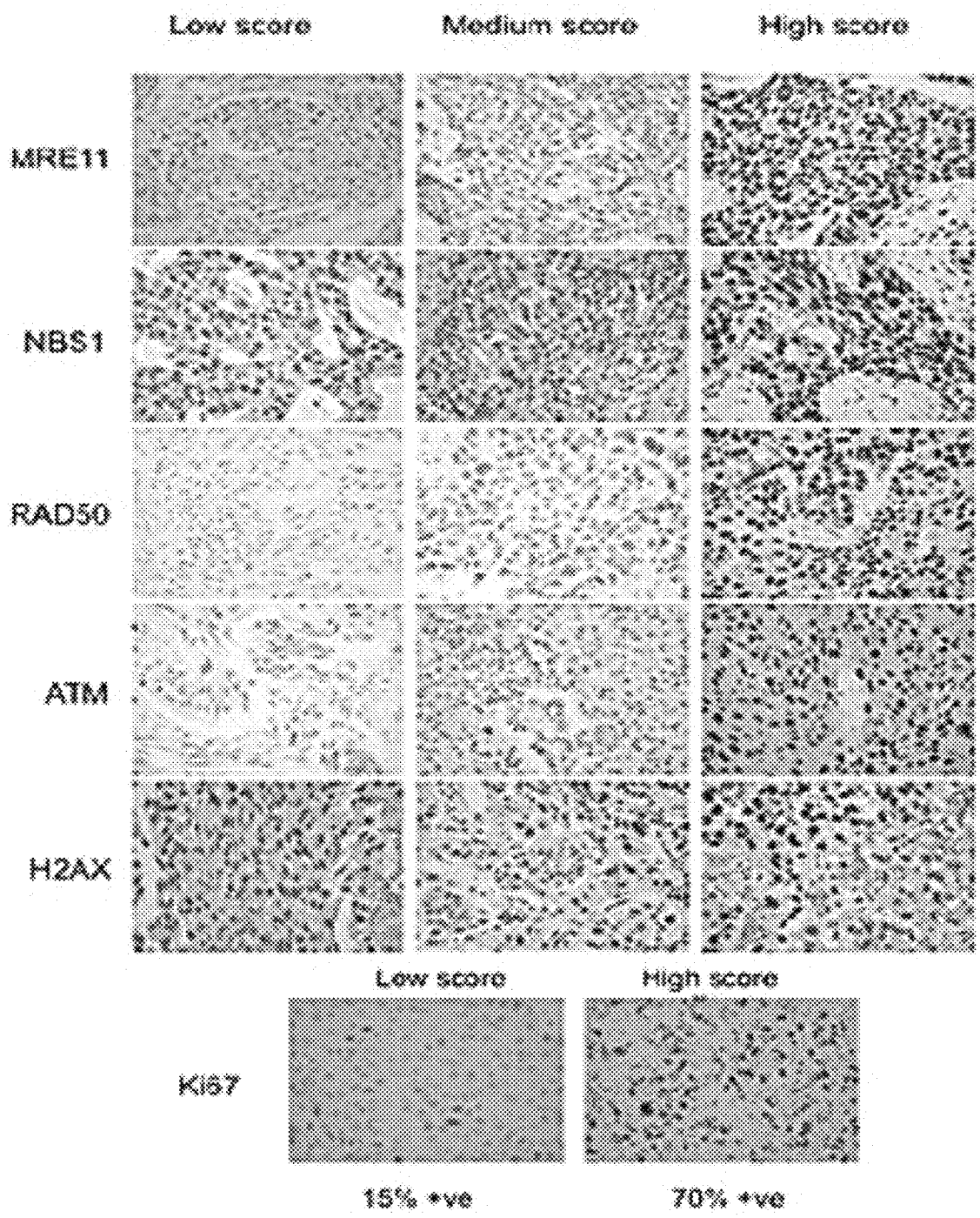
FIG. 21B is a prior art image depicting staining for MRE11, NBS1, RAD50, ATM, H2AX and Ki67 with each being divided by low, medium or high scores. (Choudhuty, A. et al., Cancer Research 70: 7017-26, 2010)
Figure 22A:
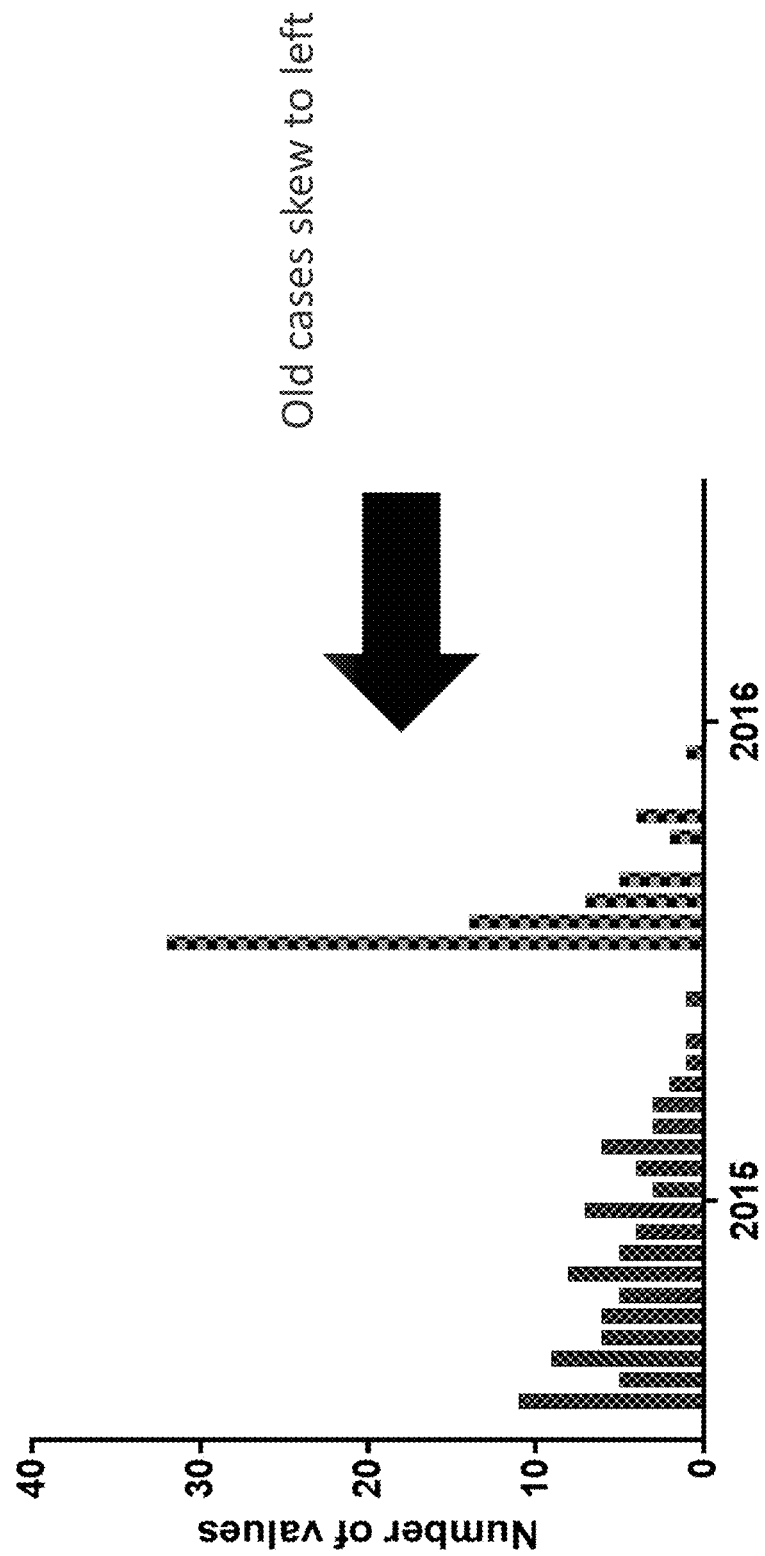
FIG. 22A is a graph depicting the MRE11 specimen type effect for MRE11 in nuclear AQUA for 2015 versus 2016.
Figure 22B:
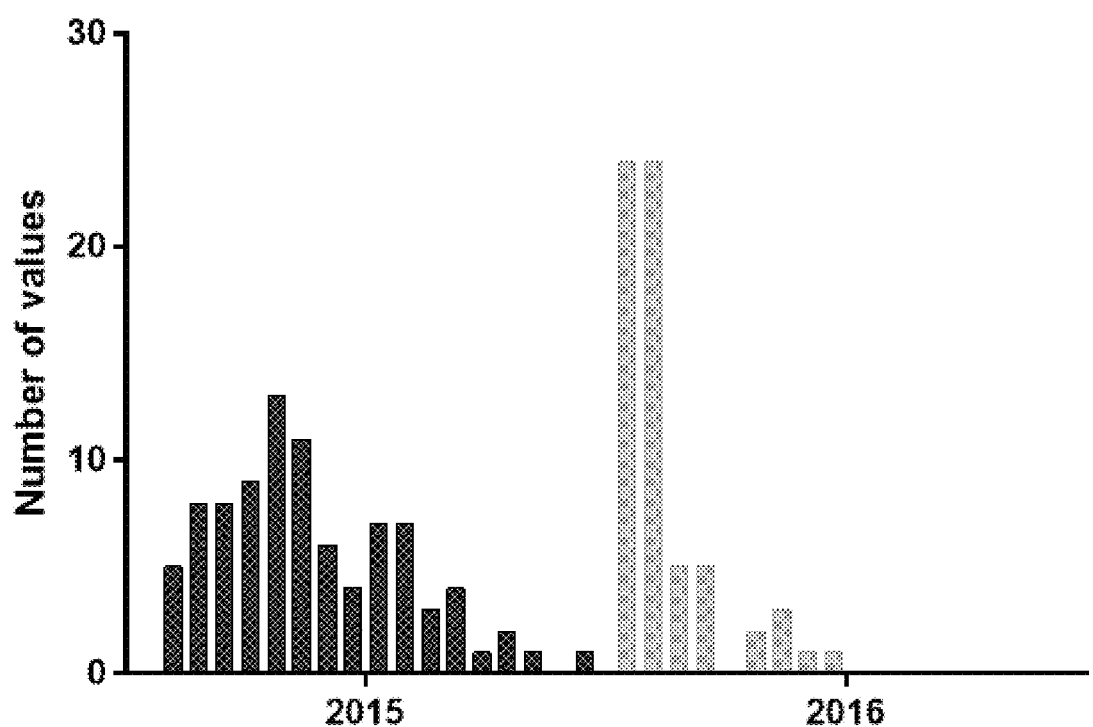
FIG. 22B is an image depicting the MRE11 specimen type effect for MRE11 in cytoplasm AQUA for 2015 versus 2016.
Figure 22C:
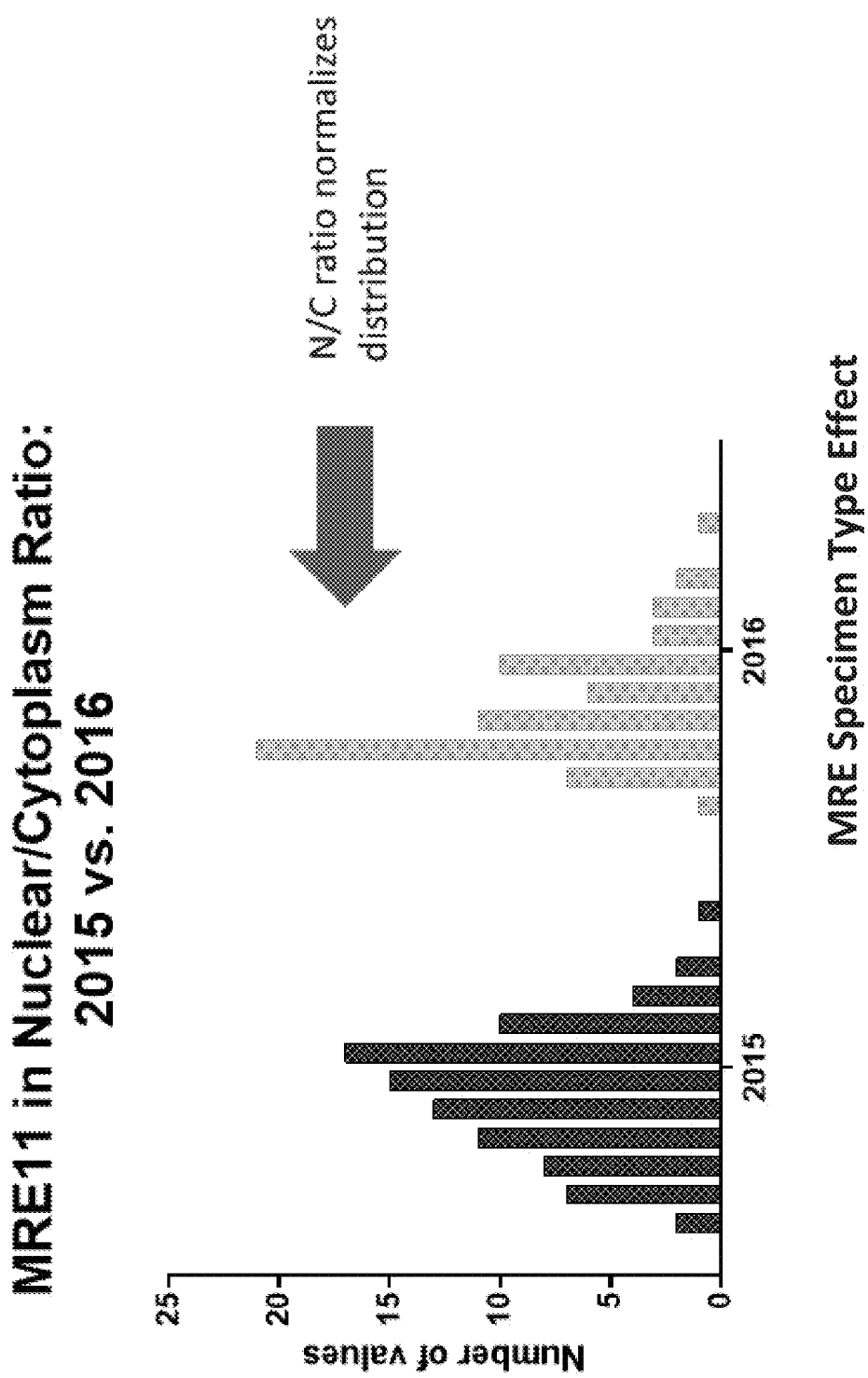
FIG. 22C is an image depicting the MRE specimen type effect for MRE11 in nuclear/cytoplasm ratio for 2015 versus 2016. As shown in the graph, nuclear/cytoplasm ratio normalizes the distribution.
Figure 23A:
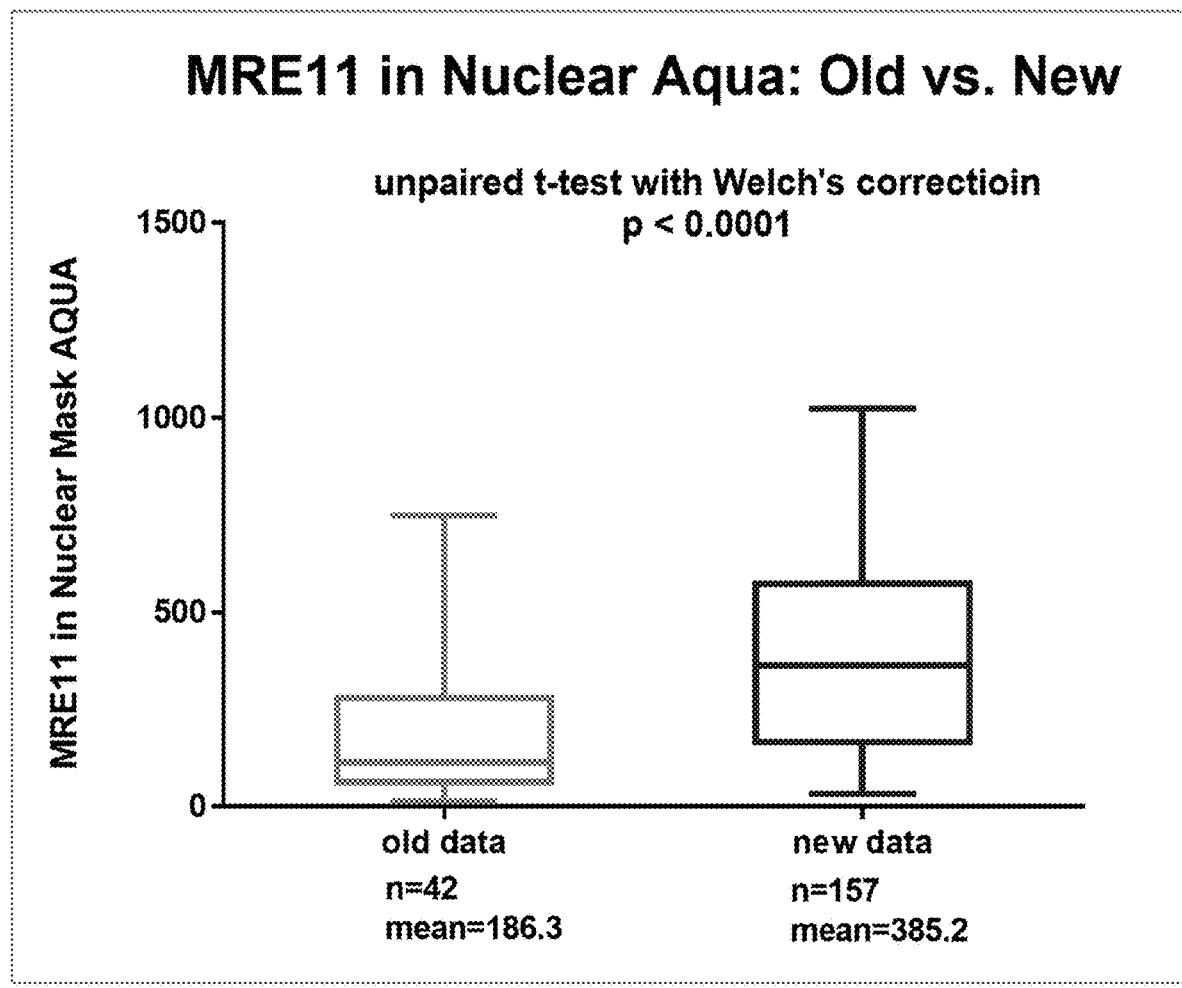
FIG. 23A is a graph depicting MRE11 in nuclear AQUA for old versus new data.
Figure 23B:
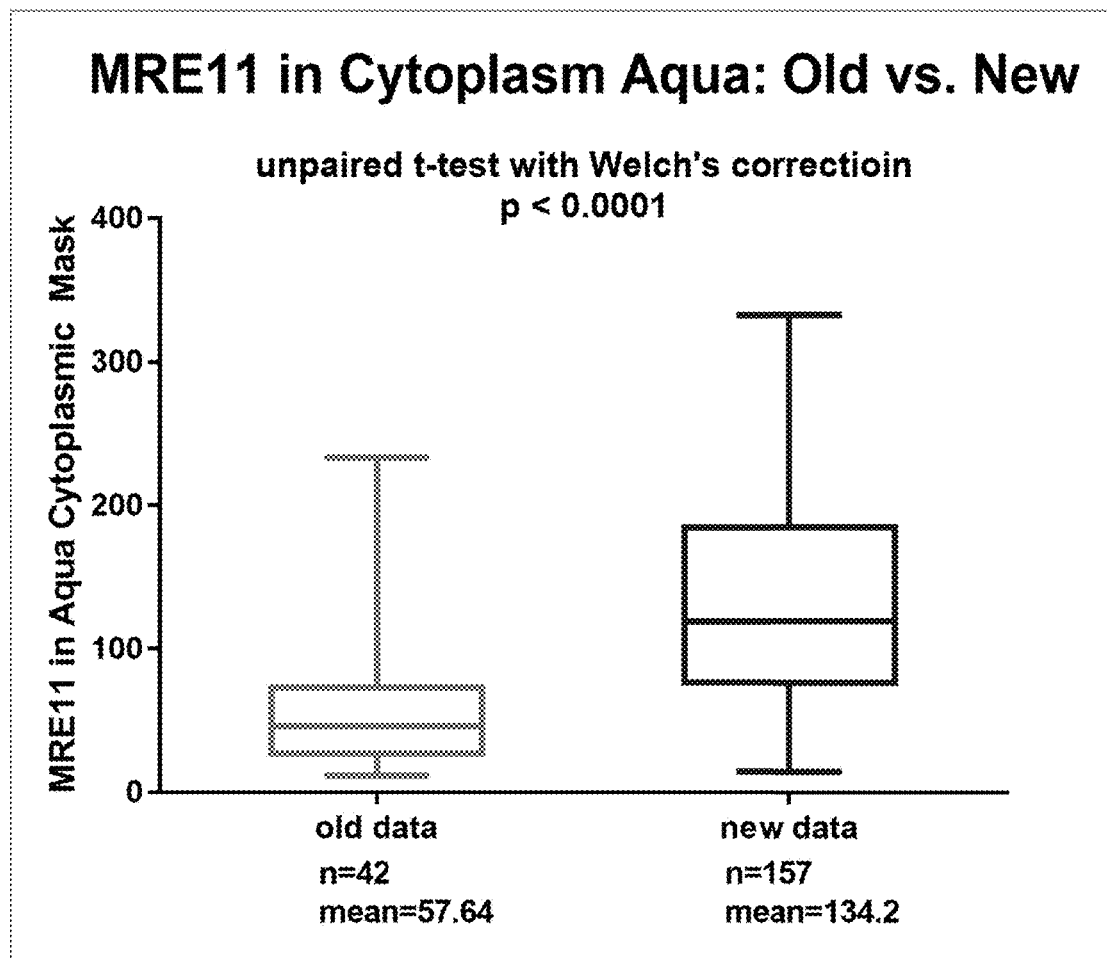
FIG. 23B is a graph depicting MRE11 in cytoplasmic AQUA for old versus new data.
Figure 23C:
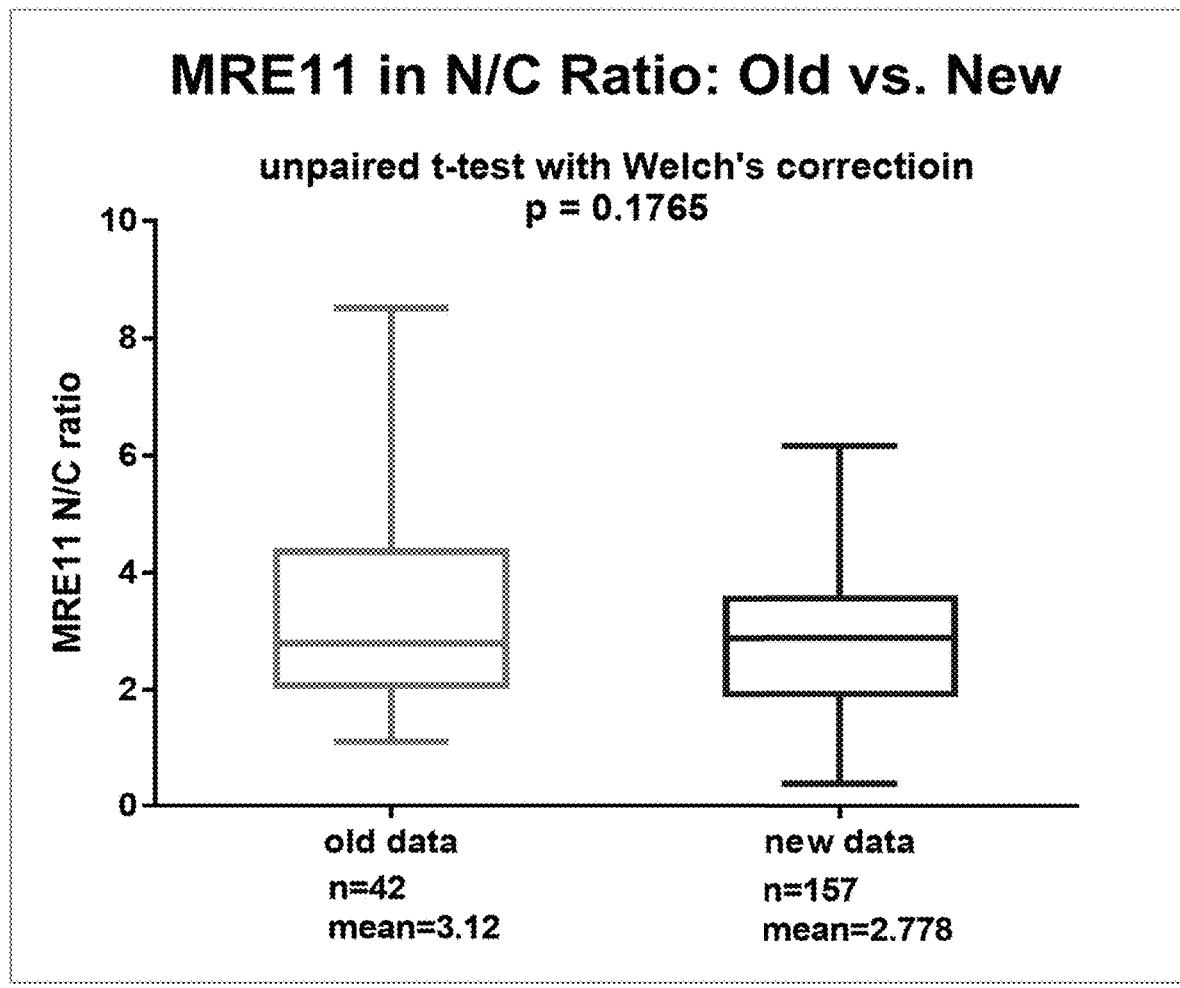
FIG. 23C is a graph depicting MRE11 in nuclear/cytoplasmic ratio AQUA for old versus new data. As shown in the graph, MRE11 AQUA N/C Ratio removes batch effect.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. Where particular values are described in the application and claims, unless otherwise stated, the term "about" meaning within an acceptable error range for the particular value should be assumed. As used herein, "about" refers to +10%.

"Subject" is used to describe an animal, preferably a mammal, more preferably a human, to whom treatment is administered, including prophylactic treatment with the compositions of the present invention. "Subject" and "patient" are used interchangeably herein.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Methods to measure protein/polypeptide expression levels of selected biomarkers in the present invention include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, mass cytometry imaging, microcytometry, microarray, microscopy, fluorescence activated cell sorting (FACS), flow cytometry, and assays based on a property of the protein including but not limited to DNA binding, ligand binding, or interaction with other protein partners.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy such as chemotherapy, such as one or more alkylating agents; radiotherapy; adjuvant therapy; surgery; or a combination thereof in order to optimize therapy for an individual subject. Cancers that express biomarkers that are indicative of a more highly aggressive cancer or poor prognosis may be treated with more aggressive therapies.

The term "treatment" or "treating" as used herein refers to the ability to ameliorate, suppress, mitigate, or eliminate the clinical symptoms after the onset of a disease state. Treatment can include chemicals, such as chemotherapeutic agents or test compounds, and/or non-chemical treatment such as radiation, electrical pulses, and magnetic fields or a combination of the two such as chemoradiation or surgical removal of the tumor or affected cancerous organ. An effective or successful treatment provides a clinically observable improvement.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes involved in cell cycle regulation, apoptosis, cell proliferation, and angiogenesis. More specifically, biomarkers of the present invention include MRE11 protein.

The term "cell" or "cells" is used synonymously herein and refers to in vitro cultures of mammalian cells grown and maintained as known in the art, as well as biological samples obtained from tumor specimens or normal specimens in vivo.

The term "nuclear score" as used herein refers to a number generated by using the measurement of MRE11 in the nucleus of the cells.

The term "cytoplasmic score" as used herein refers to a number generated by using the measurement of MRE11 in the cytoplasm of the cells.

The term "MRE11 score" or "total MRE11 score" or "MRE11 N/C score" as used herein refers to a number generated using the ratio of the nuclear score divided by the cytoplasmic score. A patient sample having a total MRE11 score above or below the determined cut point would indicate the type of therapy to be administered as well as the prognosis of the patient.

The term "masks" as used herein refers to the staining of tumor tissue for a nuclear biomarker to differentiate between tumour cells and non-tumour cells and then analyze the intensity and coverage of the staining to determine the expression of the biomarker. In general, a mask is defined as a region or area of pixels defined in one channel, i.e. all positive pixels within the DAPI channel defines areas of nuclei in an image. These mapped pixels can then be used to define what pixels are measured in another channel such as the MRE channel to determine what the MRE score is within nuclei The term "Overall Survival (OS)" as used herein refers to survival time as measured from the date of study entry/randomization to the date of death (due to any cause).

The term "Bladder-Intact Survival (BIS)" as used herein refers to the time to BIS as measured from the date of study entry/randomization to the first occurrence of either (a) cystectomy date or (b) date of death.

The term "Disease-Specific Mortality (DSM)" as used herein refers to the time to DSM as measured from the date of study entry/randomization to the date of death by bladder cancer.

The term "Clinical Complete Response (cCR)" as used herein refers to the response following induction chemoradiation.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions.

The term "baseline level" or "control level" of biomarker expression or activity refers to the level against which biomarker expression in the test sample can be compared. In some embodiments, the baseline level can be a normal level, meaning the level in a sample from a normal patient. In the instant case, normal expression is defined as the median of the score of the ratio within benign or normal cells. This allows a determination based on the baseline level of biomarker expression or biological activity, whether a sample to be evaluated for disease cell growth has a measureable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

"Low expression" as used herein refers to expression of a given biomarker below the median of normal cells. In some cases, low expression may refer to expression that is significantly (more than 50%) below the median of normal cells. The effect of low expression of a given marker on normal cell function is also considered.

The term "cut point" as used herein refers to the quantitative value assigned to an expression level of the protein below which one therapy is favored while above which a different therapy is favored. In some embodiments, the cut point refers to the lower quartile for MRE11 expression for bladder cancer patients. Patients having a total MRE11 score lower than the cut point are treated with a more aggressive form of therapy such as a cystectomy while patients having a total MRE11 score above the cut point can be treated with bladder sparing therapy such as chemoradiation therapy, chemotherapy or radiation therapy.

The term "neoplasia", "cancer", "tumor", "cancerous", and "malignant" as used herein, refer to the physiological condition in mammals that is typically characterized by unregulated cell growth or the presence of tumors. The terms are used interchangeably herein. Examples of cancer benefited by the present invention include, but are not limited to, bladder cancer; brain cancer including gliomas, breast cancer, ovarian cancer, endometrial cancer, lung cancer including non-small cell lung cancer, skin cancer including melanoma, renal cancer; oral cancer; prostate cancer; larynx cancer; thyroid cancer; colon cancer; pancreatic cancer; uterine cancer; head and neck cancer; cervical cancer; sarcomas; neuroendocrine tumors; and gastrointestinal cancers such as cancer of the esophagus, stomach, biliary system, pancreas, small intestine, large intestine, rectum and anus.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

The term "aggressive therapy" as used herein refers to surgical removal of the majority of or, in some cases, the entire organ infected with cancer. For example, in bladder cancer, a cystectomy or complete removal of the bladder would be considered an aggressive therapy.

The term "non-aggressive therapy" as used herein refers therapies such as surgical removal of a tumor that is less than the majority of the organ affected, in combination or individually with non-surgical therapies including, but not limited to, chemotherapy, radiation therapy, and chemoradiation therapy. Bladder sparing surgery plus therapy such as those listed above would be considered non-aggressive therapy.

The biological effects of low MRE11 include the inability to activate apoptosis following DNA damage. Low MRE11 may be an indicator of other molecular dysfunction identifying a separate molecular subtype of cancer, including, but not limited to, DNA repair problems, glucose metabolism problems, apoptotic deficiency, etc.

The inventors sought to measure MRE11 via IHC in invasive bladder cancer to validate MRE11 and create a CLIA certified lab for patient selection. Immunohistochemistry provides information on the expression level and localization of an antigen and has become the standard in situ assay to determine protein expression. However, immunohistochemistry is semiquantitative, subjective and highly dependent on a range of poorly controlled variables allowing different laboratories to optimize conditions by the use of variable methods that generate results that can vary between studies.

Previous work identified the lower quartile as the cut point in manual assessment of IHC. As there was no specific method to quantify staining, this cannot be applied to other data sets. While any immunohistochemical method of protein measurement used to visualize protein location may be used and is contemplated in the instant invention, including, but not limited to, mass spectrometry, hapten staining, aptamers, AQUA, the AQUA method was used to identify CLIA cut point for use in trial.

AQUA stands for Automated Quantifiable Image Analysis and is a software product used to quantitatively measure protein expression by measuring signal intensities and areas in digital images taken from fluorescently stained tissue sections. A tumor mask is first created in which binary gating allows distinction between epithelial tumors and stroma or empty space. The image is enhanced by dilating, filling holes, and removing small objects. A stain such as 4',6-diamidino-2-phenylindole (DAPI) is used to tag the nuclei. Subsequently, the DAPI image and the cytokeratin image are combined in a clustering algorithm to define compartments based on the intensity of each marker in the pixel. These compartments are then combined to provide a composite or total composite image. An image of the tumor-specific marker is taken and the sum of the intensity of the markers in all compartment pixels is divided into the subcellular compartment area on a pixel-by-pixel basis. An AQUA score (intensity/area) is generated for the target within the subcellular compartments as defined by the equation below:

$$\frac{\sum \text{target intensity in compartment pixels}}{\sum \text{compartment pixel area}} = AQUA \text{ score}$$

The resulting AQUA score can then be standardized using cell line controls with known content of the protein of interest. In AQUA, a fluorescent microscope is used to detect the expression of biomarker proteins by measuring the intensity of antibody-conjugated fluorophores within a specified subcellular compartment, such as the nucleus, cytoplasm or plasma membrane, within the tumor region of each tissue microarray spot which results in a quantitative score of immunofluorescence intensity for the tumor. (McCabe, A. et al., 2005, Automated quantitative analysis (AQUA) of in situ protein expression, antibody concentration, and prognosis, *Journal of the National Cancer Institute*, 97:24:1808-1815).

In the instant case, AQUA measures protein expression within target masks. Virtual masks are created on slides using keratin and nuclei stains and software to isolate target signals. Masks are pixels defined in a specific channel. In the DAPI channel all pixels with intensity above a defined threshold are considered positive and are used to define the x,y pixel coordinates on the stacked image. These can then map data from every other channel and define it as a nuclear data point.

The current method differs from prior methods in that AQUA is used with tumor masks to produce a precise measurement and a normalization method is used to correct for preanalytical variations. In conducting the experiments, there was a significant risk of batch effect as the specimen types were quite different, thus the inventors normalized using nuclear to cytoplasmic (N/C) ratio. The MRE N/C ratio can be computed with any computer program capable of calculating the MRE N/C ratio including, but not limited to, AQUA, HALO and DEFINIENS. This ratio gives a total MRE11 score.

The inventors also identified a specific cut point for bladder cancer that can be applied to new cases. The method output score can be used in more complex mathematical decision models including, but not limited to, PCA analysis, cluster methods, decision tree learning, and deep tree learning, to find other cut points.

While keratin was used as a mask to identify epithelial tumors herein, MRE11 ratio can also be calculated for non-epithelial tumors using different masks, including, but not limited to s100 for melanoma; Vimentin for sarcoma; GFAP for glial tumors; and synaptophysin for neuroendocrine tumors. The method allows for better selection of patients who would be responsive to surgery versus chemoradiation treatment.

MRE11 may be involved in many other tumor types, besides bladder cancer. The method described herein can be useful for other cancers given the data from TCC which show mRNA distributions having loss in several cancers including, but not limited to, breast; brain; colon; renal; uterine; head and neck; cervical; endometrial; head and neck; larynx; liver; lung; prostate; ovarian; thyroid; uterine; sarcoma; glial tumors; skin cancer including melanoma; neuroendocrine tumors; and gastrointestinal cancers such as cancer of the esophagus, stomach, biliary system, pancreas, small intestine, large intestine, rectum and anus.

Materials and Methods

Case material from RTOG Bladder Sparing Trials utilizing concurrent chemoradiation, specifically NRG/RTOG 8802, 8903, 9506, 9706, 9906 and 0233, were used with quantitative IHC-(AQUA) to measure protein with precision in specific tumor areas (nucleus and cytoplasm). Four hundred and sixty-five patients were enrolled on six RTOG bladder preserving studies all were phase II and one (RTOG 8903) was phase III. Archival tissue was available on 253 cases with 149 specimens on TMA and 104 available as unstained slides. Cases were stained with anti MRE11 antibody Rabbit mAb, clone EPR3471 (Epitomics at 1:1500 dilution). Slides were scanned on an Aperio FL instrument and analyzed via AQUA. MRE scores were determined within the nucleus (nuclear score) and cytoplasm (cytoplasmic score) of urothelial cells in the muscle invasive areas of the bladder cancer. A ratio of nuclear to cytoplasmic AQUA score (Total MRE11 score) was determined.

The inventors utilized a total MRE11 score ratio to normalize scores and overcome pre-analytical variation attributable to preparation of samples as absolute intensity of staining will be affected by factors such as ischemia, fixation duration, and time on slide between cutting and staining. While the ratio of nucleus to cytoplasm is described herein to calculate the overall score, in some embodiments, the nucleus to cytoplasm ratio of cancer cells versus normal cells may be calculated.

Staining

The ability to measure MRE11 in the nucleus and cytoplasm also depends on methods to isolate these components. In a multiplex system, a combination of stains was used including: keratin—to identify epithelial (urothelial cells); MRE11—to measure MRE11 protein in all cells; and DAPI—to identify nuclei in cells. Other nuclear stains such as histone can also be used to identify the nucleus. Each component is then acquired—the MRE11 channel, the cytoplasm channel and the nuclear channel. The cytoplasmic and nuclear channels are used to define the area for measuring the MRE11 signal intensity. Other multiplex systems can be alternatively used including, but not limited to, nanostring and mass cytometry.

The method uses DAPI and Keratin to identify regions to measure the MRE11. MRE11 is measured within nuclei within Keratin positive cells (nuclear score). MRE11 is also measured within cytoplasm of keratin positive cells (cytoplasmic score). Final N/C score is a ratio of the nuclear divided by cytoplasmic score.

The method allows precise measurement of MRE11 in all cell types in the sampled specimen and all cell compartments (nuclei of cancer cells, cytoplasm of cancer cells, and nuclei of non-cancer cells). The N/C ratio is strongly correlated to Nuclear score and Cytoplasmic score but calculating the ratio overcomes batch effect which is critical to enabling an assay to be deployed into the clinic as specimens may come at different intervals in time and cannot be analyzed as a batch. Other methods to screen/measure MRE11 are contemplated by the invention including, but not limited to, mass spectrometry, mass cytometry imaging, and nanostring.

Immunohistochemistry

4 μm thick sections were cut from patient blocks and deparaffinized in xylene, rinsed in ethanol, and rehydrated. Heat-induced epitope retrieval was performed by heating slides to 121° C. in a Citrate-based buffer (pH6) Target Retrieval Solution (Dako, Mississauga, ON, Canada) for 6 minutes in a decloaking chamber (Biocare Medical, Concord, Calif., USA). Slides were stained using a Dako Autostainer. Endogenous peroxidase activity was quenched with a 5-minute incubation of peroxidase block (Dako). Slides were washed with TBST wash buffer (Dako) and then incubated at room temperature for 30 minutes with Signal Stain protein block (Cell Signaling Danvers, Mass., USA) containing a 1:1500 dilution of MRE11 Rabbit mAb, clone EPR3471 (Epitomics). Secondary reagent Rabbit Envision+ kit (DAKO) was incubated at room temperature for 30 minutes. Next a substrate-chromagen solution (3'-diaminobenzidine tetrahydrochloride, or DAB) was applied for 10 minutes, followed by a counterstain with Hematoxylin for 2 minutes. Slides were washed with distilled water, and then dehydrated through ethanol and cleared in xylene. The tissue microarray slides were mounted with Cytoseal XYL (Thermo Scientific), and stored at room temperature until use.

Statistical Method

MRE11 was analyzed as categorical variables using its median (≤median vs. >median), lower quartile (≤Q1 vs. >Q1), and upper quartile (≤Q3 vs. >Q3) as cut points. Statistical comparisons to assess potential associations between baseline characteristics and MRE11 Nuclear/Cytoplasmic categories were carried out using the chi-square or Fisher's exact test.

OS and BIS were estimated univariately with the Kaplan-Meier method and MRE11 N/C ratio groups were compared using the logrank test. Cox proportional hazards models were used to determine if there are any associations between the MRE11 N/C ratio groups with OS and BIS. The inventors found that MRE11 N/C was not associated with OS or BIS.

DSM were estimated by the cumulative incidence method and MRE11 N/C ratio groups were compared using Gray's test. Fine-Gray regression models were used to determine if there are any associations between the MRE11 N/C ratio groups with DSM. The inventors discovered that low expression of MRE11 is associated with a significantly higher disease specific mortality (DSM).

CONCLUSION

The inventors found that low expression of MRE11 as determined by an AQUA nuclear/cytoplasmic ratio of less than 1.49 (the lowest quartile in this series) is associated with significantly higher disease-specific mortality. This study adds further evidence that MRE11 could potentially serve as a predictive chemoradiation response biomarker for selection of patients most likely to respond to radical radiochemotherapy and bladder preservation. AQUA analysis allows precise measurement of this marker in tissue samples and N/C ratio is a way to normalize measurement.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of determining therapy for a bladder cancer patient based on expression of MRE11 and treating the cancer patient comprising:
   obtaining or having obtained a sample from the patient;
   determining or having determined in the sample an expression level of MRE11 wherein the determining step comprises:
   contacting or having contacted the sample with an antibody that recognizes MRE11 protein in an immunoassay;
   detecting or having contacted the complex between the antibody and the MRE11 protein;
   determining or having determined a total MRE11 score using immunohistochemistry wherein the total MRE11 score is based on a ratio between presence of MRE11 in nucleus versus cytoplasm of cell; and
   administering cystectomy to the patient if the total MRE11 score for a calculated lower quartile is below or equal to 1.49 or administering bladder sparing chemoradiation therapy to the patient if the total MRE score for a calculated lower quartile is above 1.49.

2. The method of claim 1, further comprising the sample being measured by cytopathology, urine cytology, or circulating tumor cell test.

3. The method of claim 1, wherein the bladder cancer is muscle-invasive bladder cancer.

4. The method of claim 1, wherein the immunohistochemistry used is a multiplex system.

5. A method of predicting therapy response and treating a patient having bladder cancer based on MRE11 expression comprising:
   obtaining or having obtained a sample from the patient;
   determining or having determined in the sample an expression level of MRE11 wherein the determining step comprises:
   contacting or having contacted the sample with an antibody that recognizes MRE11 protein in an immunoassay;
   detecting or having detected the complex between the antibody and the MRE11 protein;
   determining or having determined a total MRE11 score using immunohistochemistry wherein the total MRE11 score is based on a ratio between presence of MRE11 in nucleus versus cytoplasm of cell; and
   administering bladder sparing chemoradiation therapy to the patient if the total MRE11 score for a calculated lower quartile is above 1.49 or administering cystectomy to the patient if the total MRE11 score for the calculated lower quartile is equal to or below 1.49.

6. The method of claim 5, further comprising the sample being measured by cytopathology, urine cytology, or circulating tumor cell test.

7. The method of claim 5, wherein the immunohistochemistry used is a multiplex system.

8. The method of claim 5, wherein the bladder cancer is muscle-invasive bladder cancer.

9. A method of predicting the overall survival prognosis of a patient having bladder cancer and treating the patient comprising:
   obtaining or having obtained a tissue sample from the patient;
   determining or having determined in the tissue sample an expression level of MRE11 wherein the determining step comprises:
   contacting or having contacted the sample with an antibody that recognizes MRE11 protein in an immunoassay;
   detecting or having detected the complex between the antibody and the MRE11 protein;
   determining or having determined a nuclear MRE11 score for presence of MRE11 in nucleus of a cell using immunohistochemistry;
   determining or having determined a cytoplasmic MRE11 score for presence of MRE11 in cytoplasm of the cell using immunohistochemistry;
   determining or having determined a total MRE11 score wherein the total MRE11 score is based on a ratio between the nuclear MRE11 score and the cytoplasmic MRE11 score wherein a total MRE11 score equal to or below 1.49 is indicative of a poor prognosis; and
   administering cystectomy to the patient if the total MRE11 score is equal to or below 1.49 or administering bladder sparing chemoradiation therapy to the patient if the total MRE11 score is above 1.49.

10. The method of claim 9, wherein the bladder cancer is muscle-invasive bladder cancer.

11. The method of claim 9, wherein the immunohistochemistry used is a multiplex system.

* * * * *

UNITED STATES PATENT AND TRADEMARK OFFICE
CERTIFICATE OF CORRECTION

| | |
|---|---|
| PATENT NO. | : 11,360,094 B2 |
| APPLICATION NO. | : 16/534111 |
| DATED | : June 14, 2022 |
| INVENTOR(S) | : Anthony M. Magliocco |

It is certified that error appears in the above-identified patent and that said Letters Patent is hereby corrected as shown below:

In the Specification

Column 3, Line 13 should read:
The method wherein the immunohistochem-

Column 3, Line 15 should read:
The method wherein the bladder cancer is

In the Claims

Column 14, Line 52 should read:
detecting or having detected the complex between the Signed and Sealed this
Twentieth Day of September, 2022

Katherine Kelly Vidal
*Director of the United States Patent and Trademark Office*